(12) United States Patent
Goueli et al.

(10) Patent No.: US 6,893,834 B2
(45) Date of Patent: May 17, 2005

(54) ASSAY FOR KINASES AND PHOSPHATASES

(75) Inventors: Said Goueli, Fitchburg, WI (US); Jolanta Vidugiriene, Madison, WI (US); Natasha Karassina, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 10/693,214

(22) Filed: Oct. 24, 2003

(65) Prior Publication Data

US 2004/0086954 A1 May 6, 2004

Related U.S. Application Data

(62) Division of application No. 09/871,424, filed on May 31, 2001, now Pat. No. 6,720,162.
(60) Provisional application No. 60/208,405, filed on May 31, 2000.

(51) Int. Cl.$^7$ .................................................. C12Q 1/48
(52) U.S. Cl. ............................ 435/15; 435/7.8; 435/21
(58) Field of Search ........................... 435/7.8, 7.1, 15, 435/21, 174

(56) References Cited

U.S. PATENT DOCUMENTS

| | | | |
|---|---|---|---|
| 5,527,688 A | | 6/1996 | Mallia |
| 5,869,275 A | | 2/1999 | Huang et al. |
| 6,280,965 B1 | * | 8/2001 | Rathinavelu et al. .......... 435/15 |
| 6,670,144 B1 | * | 12/2003 | Craig et al. .................... 435/21 |
| 6,720,162 B2 | * | 4/2004 | Goueli et al. .................. 435/15 |

FOREIGN PATENT DOCUMENTS

| | | |
|---|---|---|
| DE | 199 42 268 A1 | 3/2000 |
| EP | 0 444 302 A1 | 9/1991 |
| WO | WO 95/23612 A1 | 9/1995 |
| WO | WO 97/40173 A2 | 10/1997 |
| WO | WO 00/00584 A2 | 1/2000 |
| WO | WO 00/18949 A2 | 4/2000 |

OTHER PUBLICATIONS

Rao V. et al. Structure of Type IIbeta Phosphatidylinositol Phosphate Kinase. Cell Sep. 18, 1998, vol. 94 pp. 829–839.*
Chaudhary et al. (1997) Rapid purification of reporter group–tagged inositol hexakisphosphate on ion–exchange membrane adsorbers, *Bio Techniques*, 23: 427–430.

Chen et al. (1996), *J. Org. Chem.*,61:6305–6312.

Erneux et al. (1998) The diversity and possible functions of the inositol polyphosphat 5– phosphatases, *Biochimica et Biophysica Acta*, 1436 185–199.

Meahama et al. (1998) The tumor suppressor, PTEN/MMAC1, d phosphorylat s the lipid second messenger, phosphatidylinositol 3,4,5–trisphosphate, *Journal of Biological Chemistry*, vol. 273, No. 22, 13375–13378.

Ozaki et al. (2000) Intracellular delivery of phosphoinositides and inositol phosphates using polyamine carriers, *Proc. Natl. Acad. Sci. USA*, vol. 97, Issue 21, 11286–11291.

Prestwich. G.D. (1996), Touching All of the Bases: Synthesis of Inositol Polyphosphate and Phosphoinositide Affinity Probes from Glucose. *Acc. Chem. Res.* 29:503–513.

Rao et al. (1998), Phosphoinositides are Central to Signal Transduction and Membrane Trafficking in All Eukaryotes. *Cell* 94:829.

Shears, S.B. (1998) The Versatility of inositol phosphates as cellular signals, *Biochimica et Biophysica Acta* 1436: 49–67.

Wang et al. (2000) Biotinylated phosphatidylinositol 3,4, 5–trisphosphate as affinity ligand, *Analytical Biochemistry*, 280: 301–307.

* cited by examiner

*Primary Examiner*—Ralpg Gitomer
(74) *Attorney, Agent, or Firm*—Joseph T. Leone, Esq.; Dewitt Ross & Stevens S.C

(57) ABSTRACT

Disclosed is a method and corresponding kit for assaying the presence, activity, or both, of an enzyme classified within an enzyme classification selected from the group consisting of EC 2.7.1, EC 3.1.3, and EC 3.1.4. The method generally includes the steps of reacting an enzyme with a substrate for a time sufficient to yield phosphorylated or dephosphorylated product; contacting the product with a binding matrix, whereby product is adhered to the matrix; and then analyzing the matrix for presence of, amount of, or both the presence and the amount of the product fixed to the matrix, whereby the presence, the activity, or both the presence and activity of the enzyme can be determined.

17 Claims, 11 Drawing Sheets

ASSAY FOR KINASES AND PHOSPHATASES

PRIORITY co-pending application Ser. No. 09/871,424, filed 31 May 2001, which claims priority to provisional application Ser. No. 60/208,405, filed 31 May 2000, the entire content of which is are incorporated herein.

This application is a divisional application of Application Ser. No. 09/871,424 filed May 31, 2001, now US Pat. No. 6,720,162, which claims benefit of.

FIELD OF THE INVENTION

The invention is directed to assays for determining the presence, activity, or both, of kinases and phosphatases. The preferred method is an assay for lipid kinases, phospholipid kinases, and phospholipid phosphatases.

DESCRIPTION OF THE RELATED ART

The importance of phospholipids in general, and phosphoinositides in particular, in the regulation of cellular processes such as cell proliferation, apoptosis, and secretory functions has been recognized for a number of years. While the importance of these compounds is manifest, there is much that remains unknown about how these important cell-signaling compounds are regulated.

Phosphoinositides have the general formula shown in 1:

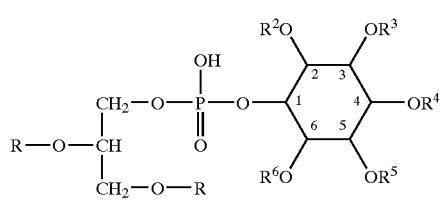

where each R is an unsubstituted or substituted alkyl, alkenyl, alkylcarbonyl, or alkenylcarbonyl group and $R^2, R^3, R^4, R^5$ and $R^6$ are hydrogen atoms and their locations on the inositol moiety. These hydrogen atoms can be replaced by phosphate groups singly or in various combinations. The general structure 1 shall be referred to herein as a phosphoinositide, or simply a "PI." Where relevant, the presence and position of phosphate groups on the inositol moiety will be designated by a number designation followed by the letter "P." So, for example, a PI with a phosphate in the $R^3$ position (i.e., phosphatidylinositol-3-phosphate) will be designated "PI3P," phosphatidylinositol-4-phosphate will be designated "PI4P," etc. For multiply phosphorylated PI's, numbers separated by a comma will be used to designate the positions of the phosphate groups. For example, "PI3,4P$_2$" designates a PI which is phosphorylated at the $R^3$ and $R^4$ positions of the inositol moiety as shown in 1. Phosphorylated PI's in general are referred to as "PIP's"

Because PI's are thought to be central to signal transduction and membrane trafficking in all eukaryotes (Rao et al. (1998) *Cell* 94:829), an understanding of the enzymes that regulate PI's, PIP's, and their metabolites would be extremely helpful. The present invention, an assay to determine the presence and/or activity of lipid kinases, phospholipid kinases, and phosphatases can be used to elucidate further the biological role of PI's.

Any number of assays for measuring enzyme activity are known in the prior art. In particular, Huang et al., U.S. Pat. No. 5,869,275, issued Feb. 9, 1999, describes an affinity ultrafiltration-based assay for measuring protein transferase activity. In this approach, labeled and unlabeled substrate having a binding site (the binding site either being created by action of the enzyme being assayed or which exists as an integral part of the substrate, such as an antigenic determinant) are incubated with the enzyme to form labeled product and unlabeled product. The reaction mixture is then contacted with a soluble macroligand capable of forming a specific complex with the product. Of critical importance is that the size of the macroligand-product complex must be significantly larger than the size of any contaminants or reactants found in the reaction mixture The macroligand-product complex is then separated from reactants via ultrafiltration. The critical consideration here is that the nominal molecular weight limit of the ultrafiltration membrane must be larger than any potential contaminants in the reaction mixture, as well as larger than any unreacted, labeled substrate, yet smaller than the size of the macroligand-product complex. In this fashion, reactants and contaminants pass through the membrane, while the much larger macroligand-product complex is retained by the membrane. Examination of the ultrafiltration retentate for the presence of labeled product provides an indication of the extent of the reaction.

Mallia, U.S. Pat. No. 5,527,688, issued Jun. 19, 1996, describes assays for protein kinases in which a binding membrane is suspended within a reaction vessel, thereby dividing the vessel into two compartments. By adhering products to the suspended membrane, washing can be accomplished centrifugally by placing the wash solution in the upper chamber and centrifuging, thereby forcing the wash solution through the membrane.

SUMMARY OF THE INVENTION

The invention is an assay and a corresponding kit for determining the presence and activity of kinases and phosphatases, and, more specifically, lipid and phospholipid kinases and phosphatases. The preferred embodiment of the invention is an assay capable of measuring the presence and/or activity of any kinase or phosphatase which adds or removes a phosphate group from a lipid or phospholipid substrate.

In particular, a first embodiment of the invention is directed to a method for assaying the presence, the activity, or both the presence and the activity, of an enzyme falling within the enzyme classifications EC 2.7.1, EC 3.1.3, and EC 3.1.4. The method comprises first reacting the enzyme with a corresponding substrate for a time sufficient to yield phosphorylated product when assaying a kinase or a dephosphorylated product when assaying a phosphatase. The reaction, of course, is run under conditions which render the enzyme under investigation active, and thus the enzyme will catalyze either a phosphorylation (kinase) or a dephosphorylation (phosphatase) of the substrate.

The product formed by the enzymatic reaction is then contacted with a binding matrix. This results in product being bound or fixed to the matrix. With the product fixed on the matrix, the matrix can be mechanically separated from the reaction solution, thereby providing an easy means to separate the products of the enzymatic reaction from unreacted reactant, enzyme, and other non-product ingredients of the reaction solution.

The matrix is then analyzed for the presence of, the amount of, or both the presence and the amount of, the product fixed to the matrix. By determining the presence and/or amount of the product found on the matrix, the presence, the activity, or both the presence and activity of the enzyme that gave rise to the products can be determined.

A second embodiment of the invention is directed to a method as substantially described above, with the addition that the substrate includes a binding moiety. When the substrate is converted into product (by the action of the enzyme), the product also contains the binding moiety.

The product is then contacted with a binding matrix that specifically binds for the binding moiety. This results in product being specifically fixed to the matrix (via the interaction of the binding moiety and the binding matrix. The preferred binding moiety is biotin and the preferred binding matrix is avidin or streptavidin immobilized on an inert support. The matrix is then analyzed as in the first embodiment.

In the second embodiment of the invention, the approach used to modify the lipid or phospholipid enzyme substrate is to include a binding moiety. In this embodiment, the binding moiety (and the binding moiety alone) will bind specifically to a support designed for that purpose. In this fashion, products bearing the binding moiety can be separated easily from products which do not bear the binding moiety by simply passing the reaction mixture over the support. It is much preferred that the binding moiety be biotin. The support would then comprise any suitable substrate (beads, filter paper, etc.) having avidin or streptavidin immobilized thereto.

In a third embodiment of the invention, a support is not required. In this approach, the assay is conducted entirely in the liquid phase. Using a biotin binding moiety as an example, the avidin or streptavidin would be added to the reaction and the biotin-avidin complexes which form could be separated by any known means (electrophoresis, chromatography, centrifugation, etc.).

In short, the assay of this embodiment functions to determine the presence and activity of lipid and phospholipid kinases as follows: A lipid or phospholipid substrate for the enzyme to be assayed is first modified to include a binding moiety. As noted above, the binding moiety is preferably biotin, although an antibody or antigen can also be used as the binding moiety. Regardless of the choice of binding moiety, it is important that the binding moiety be attached to the substrate in such a fashion that its presence does not interfere with the enzyme's ability to phosphorylate or the substrate. In most instances, this requires that the binding moiety be added to the end of one of the fatty acyl moieties of the substrate because recognition is dictated largely by the nature of the headgroup.

To assay for lipid and/or phospholipid kinases, the modified substrate is exposed, in the presence of $\gamma$-$^{32}$P ATP, to a solution thought to contain the kinase of interest and allowed to incubate for a sufficient amount of time and under appropriate conditions such that the kinase, if present and active, can phosphorylate the modified substrate with a $^{32}$P-labeled phosphate group. The reaction mixture is then contacted with a capture membrane or matrix, that is, a support bearing a moiety which will capture specifically the modified substrates; in the case of biotin, this would be avidin or streptavidin linked to a support. If binding moiety is an antigen, the capture membrane would include immobilized antibodies specific for the antigen, etc.

When the modified substrates are captured to a solid support, free $^{32}$P ATP, reactants, contaminants, etc., are gently washed from the support and the bound radiolabeled material is measured for radioactivity using a scintillation counter, a "PhosphoImager" device, or by autoradiography.

Where phosphatases are to be assayed, the assay protocol is the same as noted above, with the exception that the substrate is modified to include $\gamma$-$^{32}$P phosphate groups. In addition, an unlabeled substrate can be used and the released phosphate determined with a colorimetric method or a fluorescent method. (For example, Molecular Probes, Eugene, Oreg., sells a method for fluorescent detection of a released phosphate.) The action of the phosphatase enzyme under analysis will then remove a portion of those groups. In this approach, the reduced activity found on the matrix as compared to the starting labeled substrates is a direct measure of the activity of the phosphatase, or, in the case of non-radiolabeled phosphate, the amount of released phosphate is used as a measure of phosphatase activity.

The invention also comprises a corresponding kit that contains all of the necessary reagents to carry out the assay one or more times. The kit generally comprises: an amount of reaction buffer disposed in a first container; an amount of substrate for an enzyme classified within an enzyme classification selected from the group consisting of EC 2.7.1, EC 3.1.3, and EC 3.1.4, the substrate disposed in a second container; an amount of purified enzyme classified within an enzyme classification selected from the group consisting of EC 2.7.1, EC 3.1.3, and EC 3.1.4, the enzyme disposed in a third container (or the enzyme can be supplied by the user); an amount of binding matrix; and instructions for use of the kit.

A distinct and primary advantage of the assay is that is allows investigators to assay the activity of any number or type of lipid or phospholipid kinases or phosphatases quickly and conveniently.

Another primary advantage of the assay is that it is sufficiently sensitive to assay lipid and phospholipid kinases and phosphatases directly from tissue and cell extracts. Due to the high affinity of the lipid and phospholipid products to the matrix, extraneous free $\gamma^{32}$P-ATP can be removed by washing and the amount of product formed can be determined without need for lipid extraction. This is a distinct improvement over conventional HPLC and TLC assays, which require lipid extraction. Eliminating lipid extraction, which is costly and time-consuming, makes the subject assay very attractive to investigators in this field.

Another advantage is that the assay is scalable to accommodate high throughput formats. The assay is highly amenable to automation.

μg) (lanes 3 and 4) or PI (50 μg) (lanes 1 and 2) as reaction substrates. Samples were processed using the conventional phospholipid extraction procedure illustrated in FIG. 1 (lanes 2 and 4) or according to the present invention (lanes 1 and 3).

Figure 3:
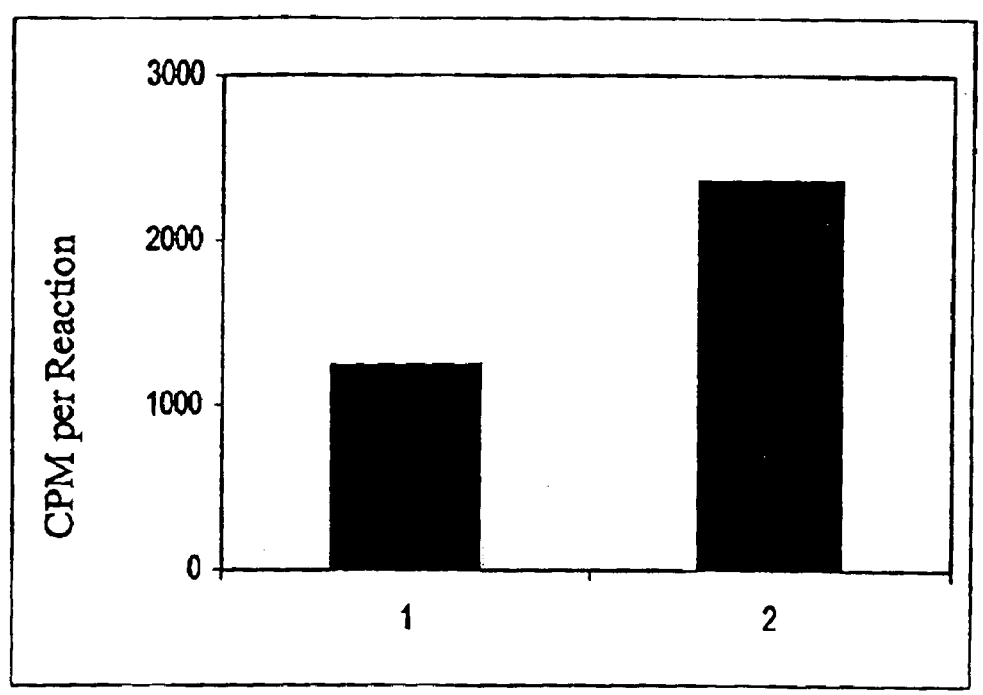

FIG. 3: Detection of PI-3K activity associated with activated receptor. 3T3NIH cells (5×10$^7$ cells) were treated without (lane 1) or with (lane 2) PDGF (50 ng/ml for 5 min at 37° C.) and PI-3K was co-immunoprecipitated using anti-phosphotyrosine specific antibodies. The PI-3K reactions were run for 60 min using PIP$_2$ (10 μg)+PS (20 μg) as substrates.

Figure 4A:
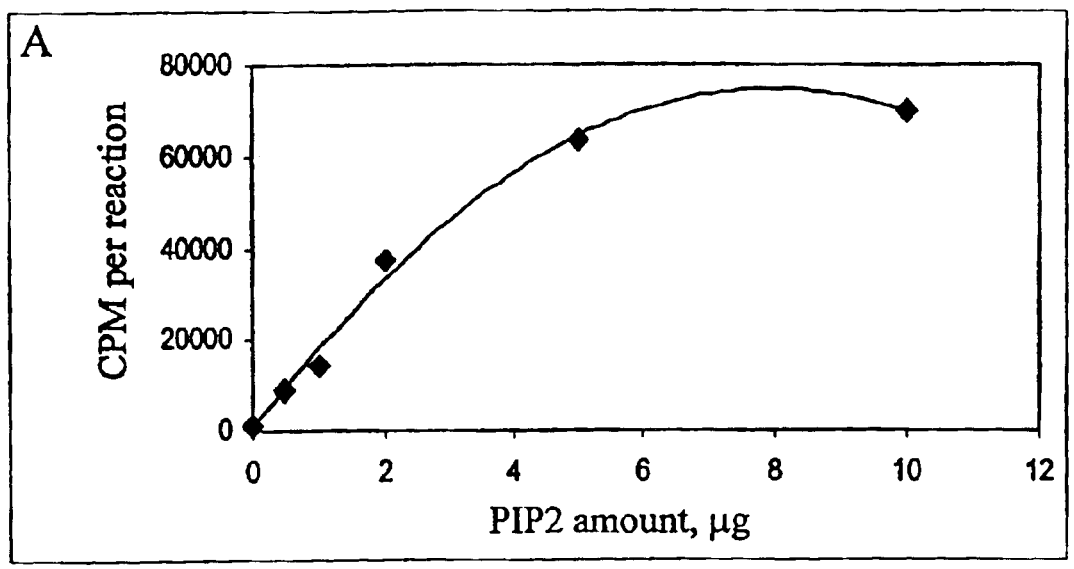
Figure 4B:
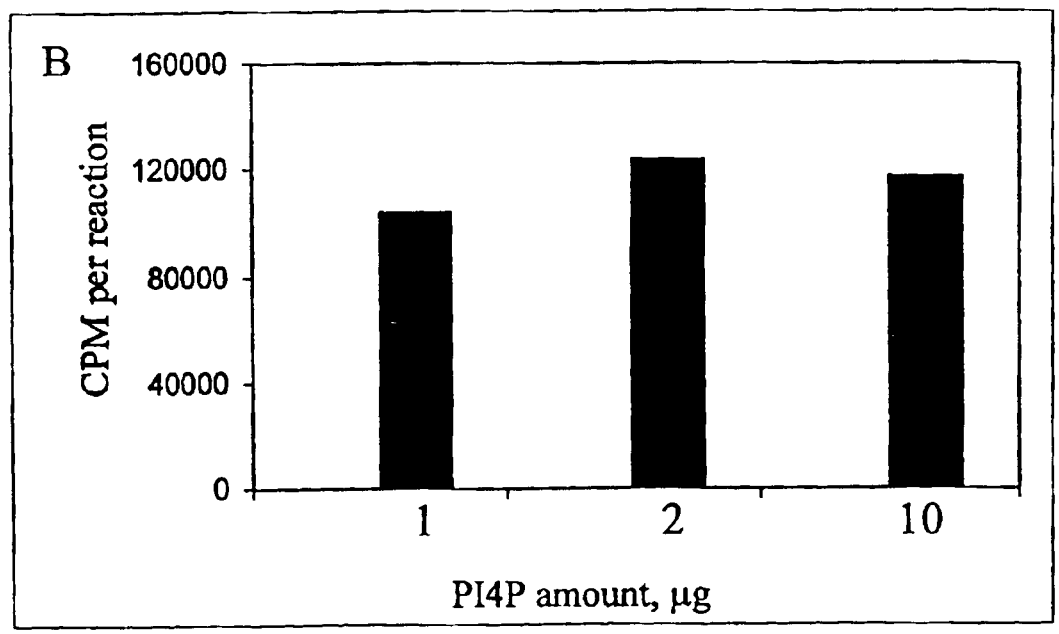

FIGS. 4A and 4B: Dependence of PI-K activity on the amount of lipid substrate loaded on the membrane. FIG. 4A: PI-3K activity was measured using PI-3K from Alexis Biochemical (San Diego, Calif.) (12.5 μg/ml) for 60 min at room temperature. FIG. 4B: PI-5K activity was measured using purified PI-5K (125 ng/ml) for 60 min at room temperature. In addition to lipid substrates, all samples contained 10 μg of PS loaded on the membrane.

Figure 5A:
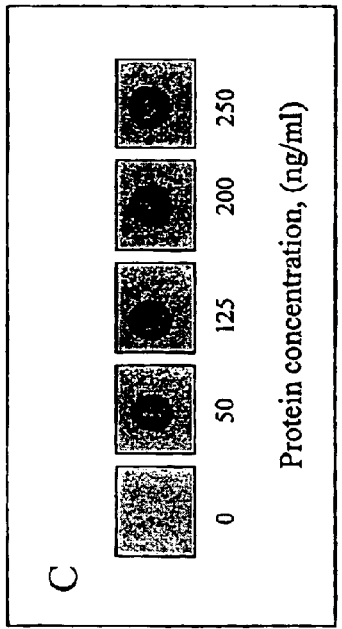
Figure 5C:
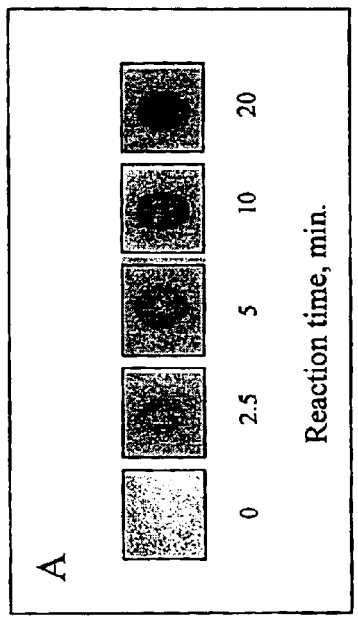
Figure 5B:
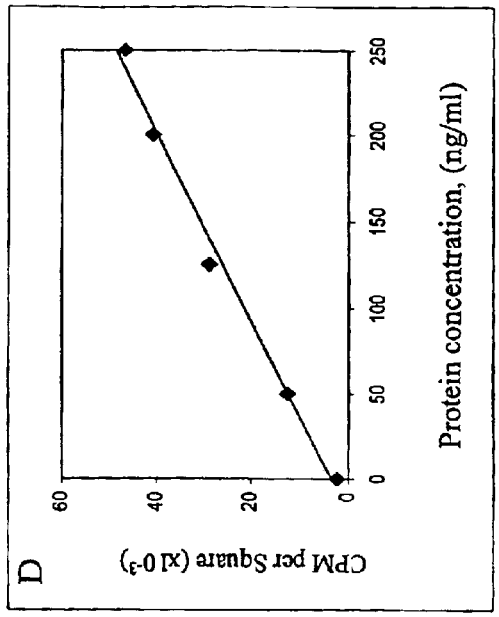
Figure 5D:
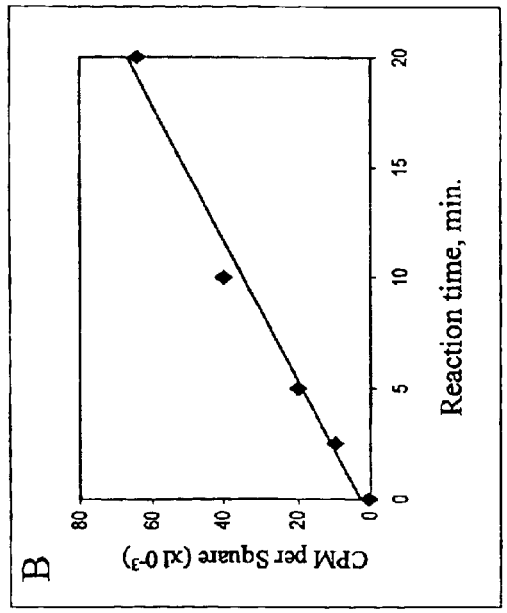

FIGS. 5A, 5B, 5C, and 5D: Linear detection of PIP-5K activity using the present invention. Assays were performed using the inventive method described herein, utilizing 3 μl of a lipid mixture containing 1 μg of PI4P and 10 μg of PS in chloroform/methanol 2:1 spotted onto a pre-numbered membrane square. FIGS. 5A and 5B: PI-5K activity was measured at different time points using 4 ng of purified protein. FIGS. 5C and 5D: PI-5K activity was measured for 10 min using different protein concentrations. The reaction products were analyzed by phosphorimaging (FIGS. 5A and 5C) or by scintillation counting (FIGS. 5B and 5D). Summary: Between 20 pmol to 1.2 nmol of formed product can be detected using the present invention.

Figure 6A:
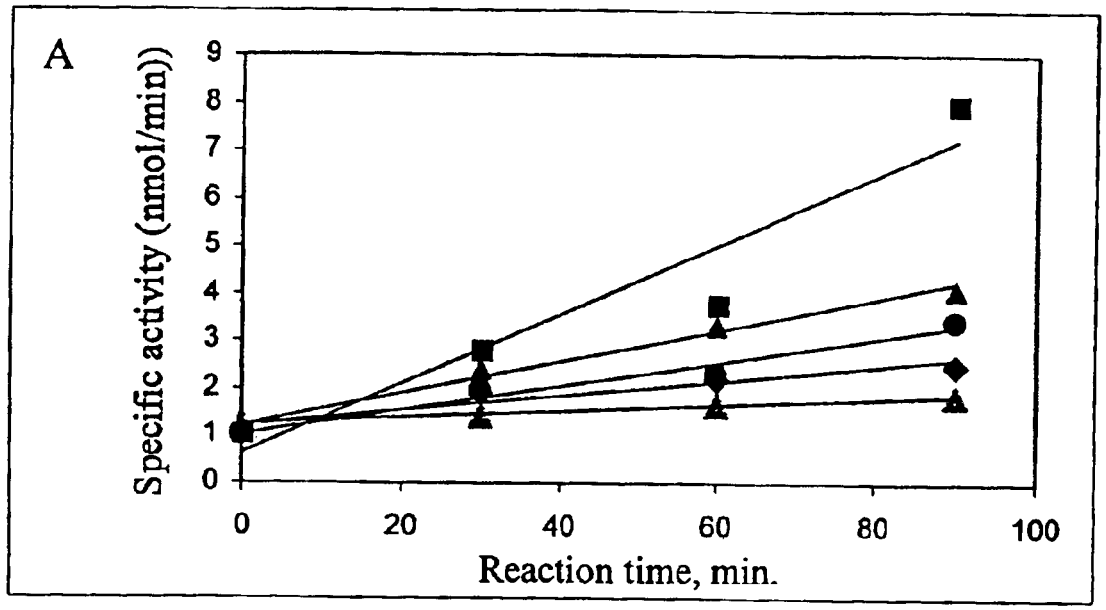
Figure 6B:
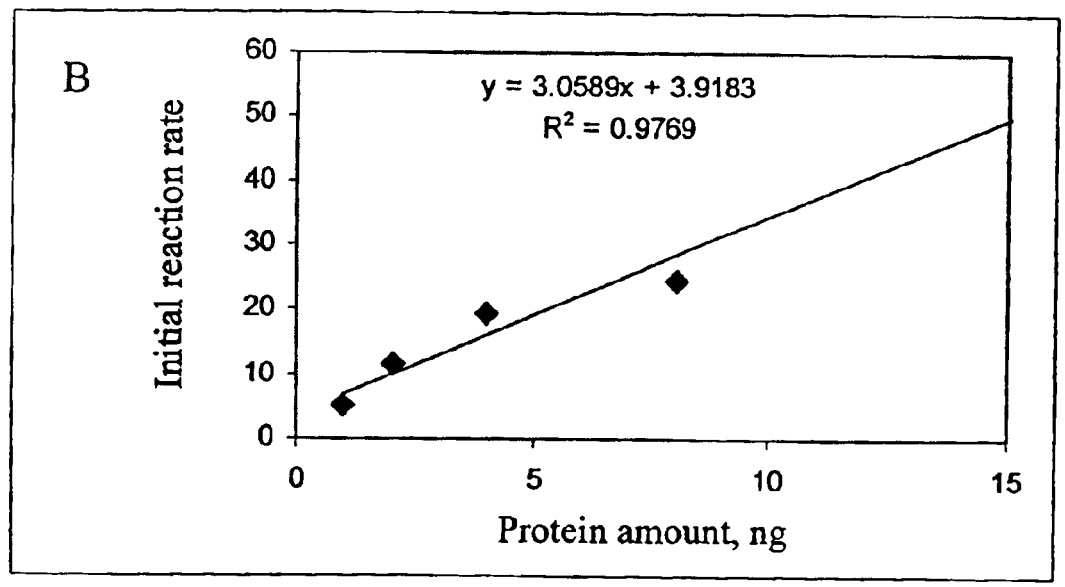

FIGS. 6A and 6B: Linear detection of PI-3K activity using the present invention. Assays were performed using the inventive method described herein, utilizing 5 μl of PI (25 μg) in chloroform/methanol 2:1 spotted onto a well of a "SAM2"-brand membrane 96-well plate. Assays were performed using decreasing amounts of partially-purified PI-3K: 1 ng, 2 ng, 4 ng, 8 ng, and 16 ng. Based on obtained scintillation counts, the specific activity has been calculated and shown in FIG. 6A. The calculated initial reaction rate for different amounts of protein is shown in FIG. 6B.

Figure 7A:
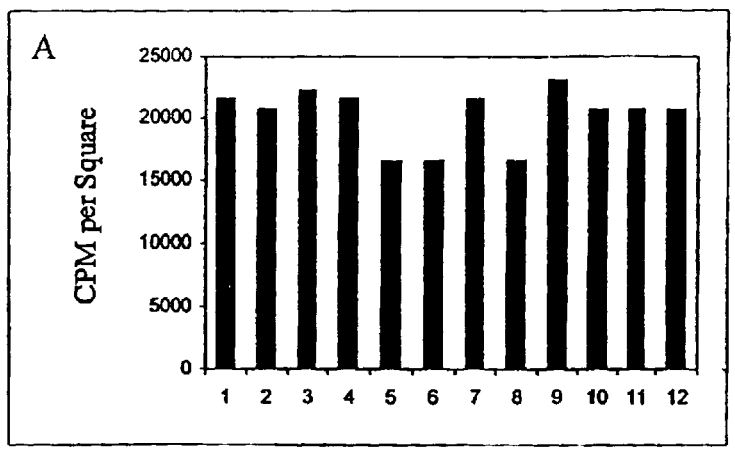
Figure 7B:
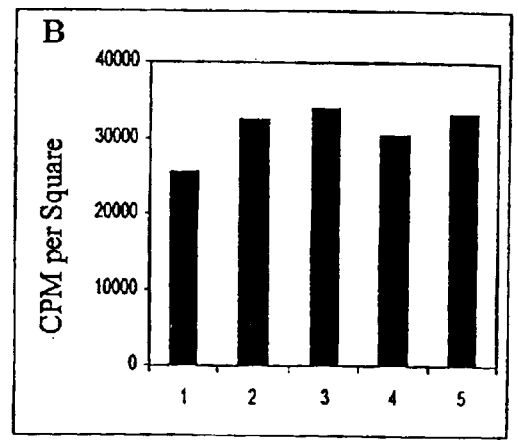
Figure 7C:
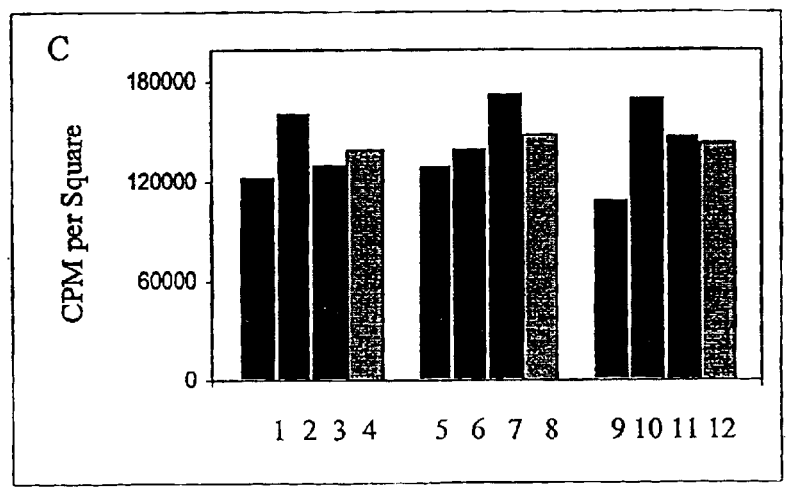

FIGS. 7A, 7B, and 7C: Reproducibility of the subject invention. Assays were performed using: (FIG. 7A) partially purified PI-3K (500 ng/ml) and PIP$_2$ (10 μg)+PS (20 μg) as lipid substrates for 40 minutes; (FIG. 7B) PI-5K (125 ng/ml) and PI4P (1 μg)+PS(10 μg) for 15 minutes; (FIG. 7C) PI-5K (125 ng/ml) and PI4P (1 μg) for 60 minutes. All assays were performed at room temperature using 1 μCi of $^{32}$P-ATP. In FIG. 7C, the reactions were carried out on three different plates (samples 1–4; 5–8; 9–12, respectively). In each plate the reactions were done in triplicates at three different locations. Each point represents the average of three independent reactions. Lighter bars show the average of 9 points done on the same plate.

Figure 8:
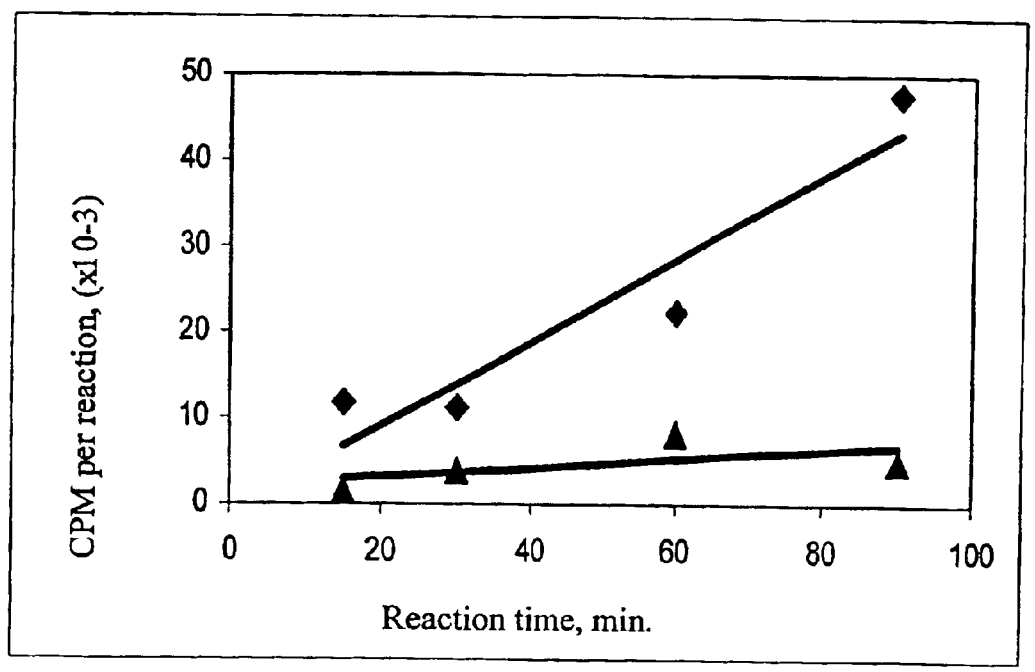

FIG. 8: Inhibition of PI-3K activity. Reactions according to the present invention were performed using partially-purified PI-3K for different periods of time in the presence (triangles) or absence (diamonds) of the PI-3K inhibitor wortmannin (final concentration 100 nM).

Figure 9:
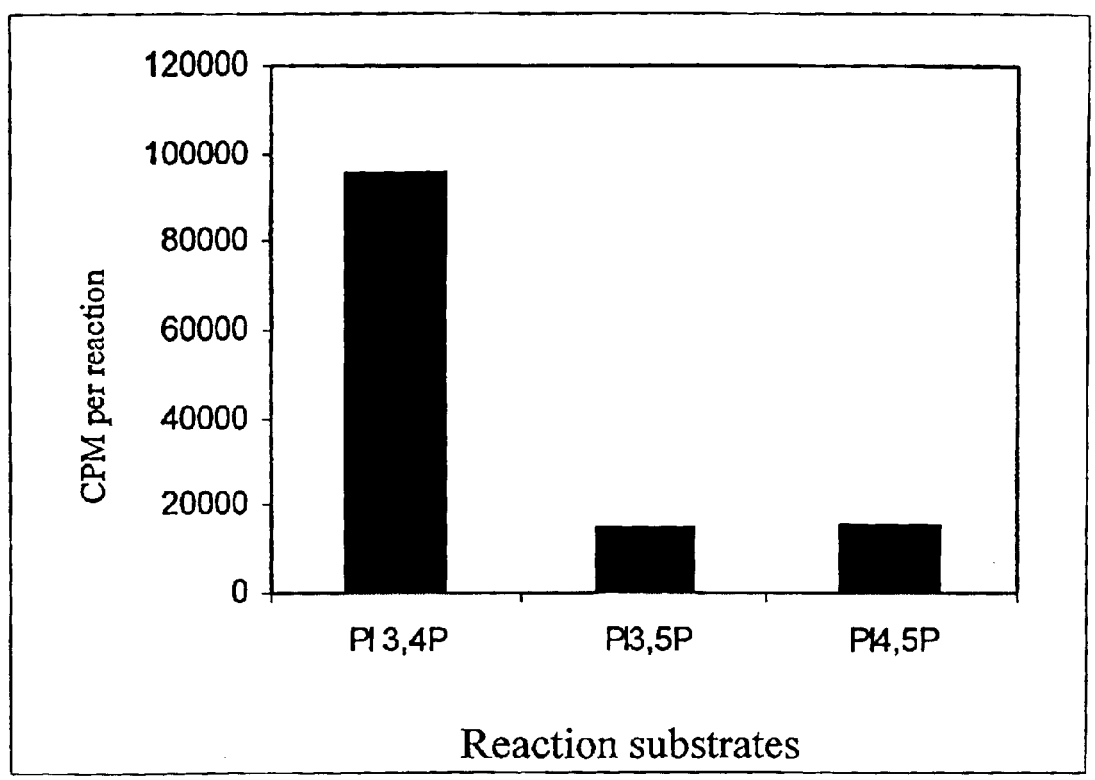

FIG. 9: Reaction specificity toward lipid substrates. Reactions according to the subject invention were performed with purified PI4P-5K (250 ng/ml) for 45 min at room temperature using 1 μg of different lipid substrates: PI3,4P (lane 1); PI3,5P$_2$ (lane 2) and PI4,5P$_2$ (lane 3). In addition to lipid substrates, all samples contained 10 μg of PS loaded on the membrane.

Figure 1:
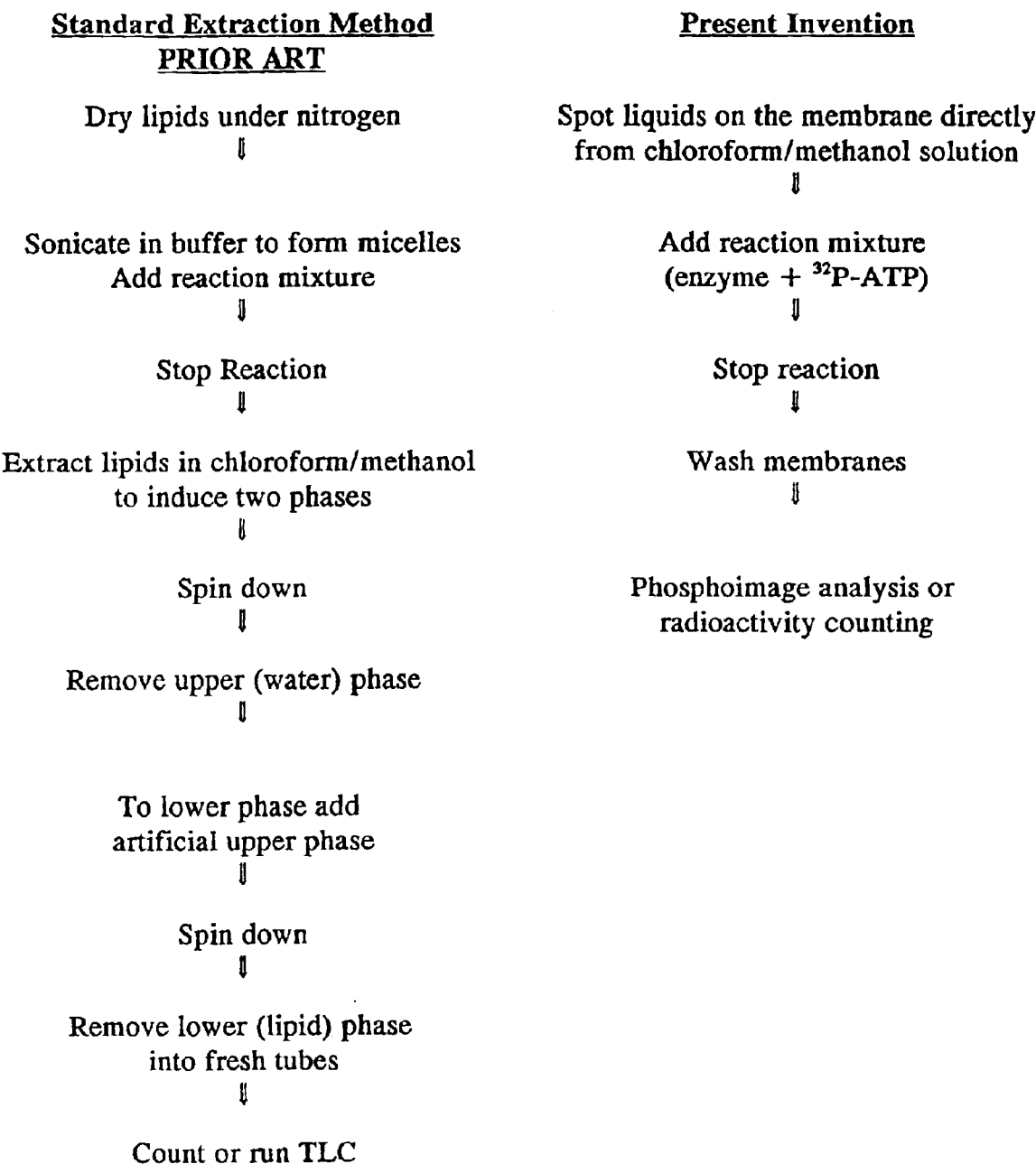
FIG. 1: Flow chart. Parallel flow charts comparing prior art methods to a preferred method according to the present invention.
Figure 10:
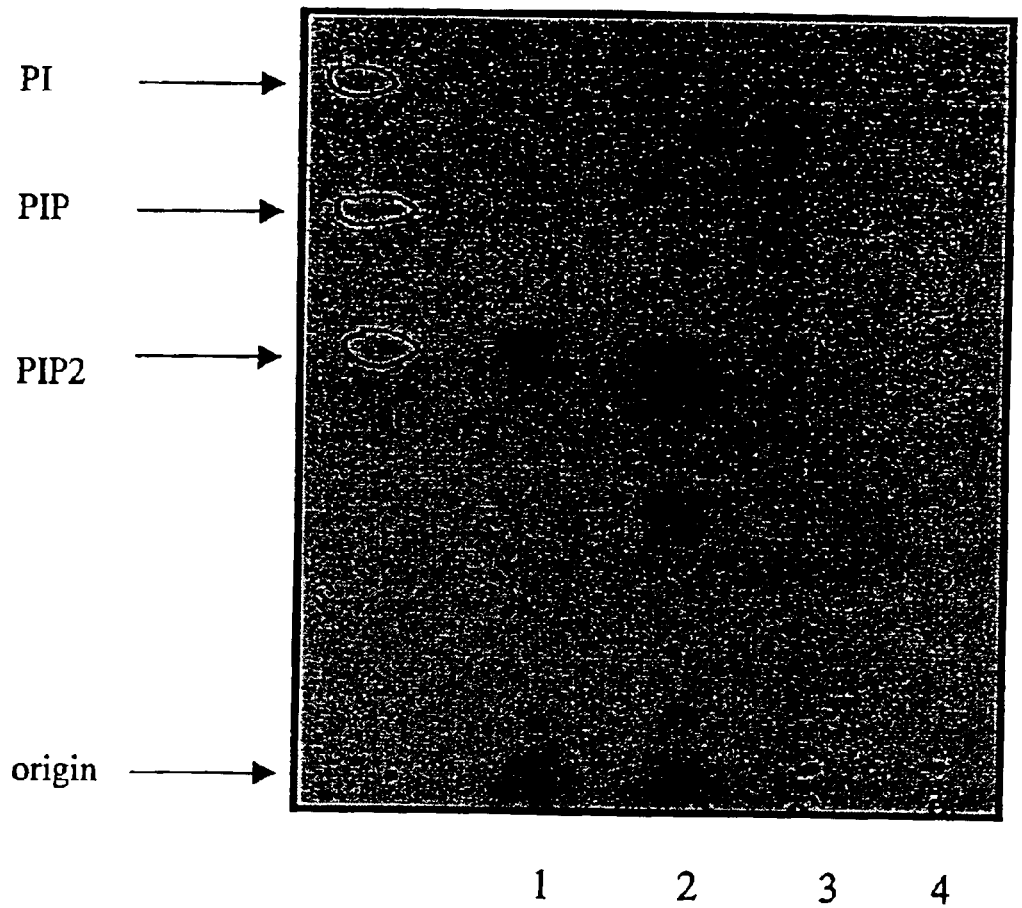

FIG. 10: Comparison of reaction products: the present invention vs. the conventional phospholipid extraction procedure. Activities were assessed using 1 μg of PI4P+10 μg of PS as reaction substrates and purified PI-5K (2.5 ng) as the enzyme. The reaction was carried out for 10 minutes (lanes 1 and 2) and 0 minutes (lanes 3 and 4). The reaction was worked up using the conventional phospholipid extraction procedure as illustrated in FIG. 1 (lanes 2 and 4) or according to the subject invention (lanes 1 and 3). When the reaction was been performed on membrane sheets, 40% of bound reaction products were re-extracted for TLC analysis.

Figure 11A:
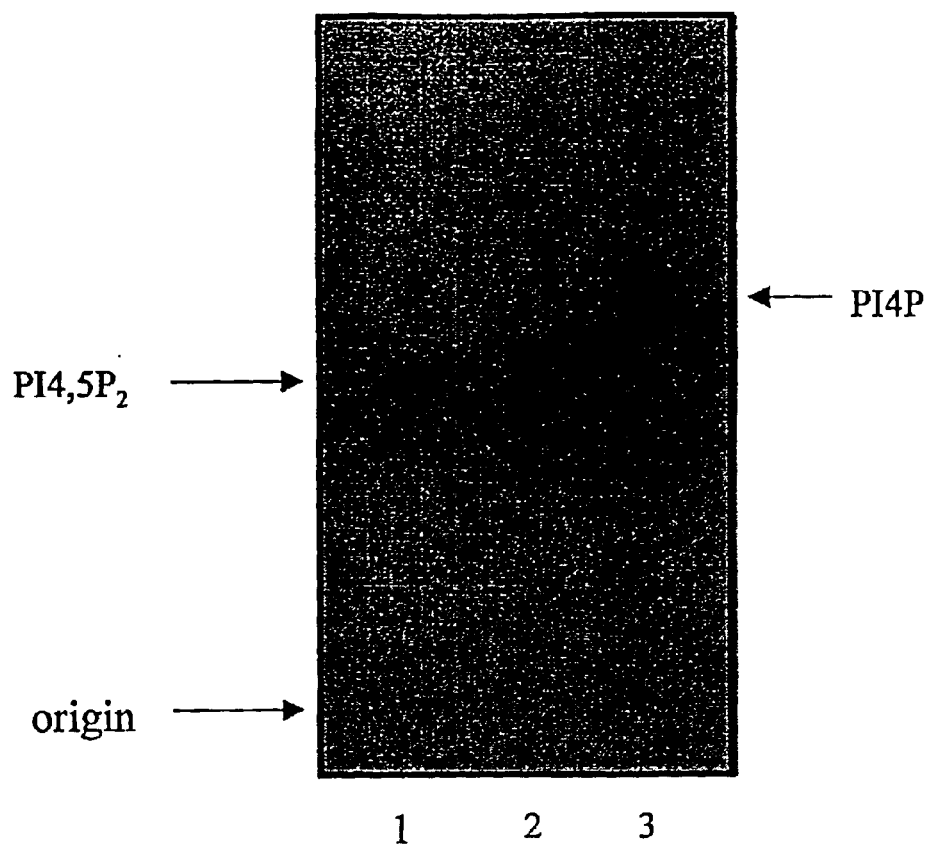

FIG. 11A: Comparison of PI4P-5 kinase activity using biotinylated and non-biotinylated short-chain lipids and non-biotinylated long-chain lipids. PI4P-5 kinase activity was measured using PI4P-C$_6$-biotin (lane 1), PI4P-C$_8$ (lane 2) and PI4P-C$_{16}$ (lane 3) as reaction substrates. The reaction products were extracted and analyzed via TLC.

Figure 11B:
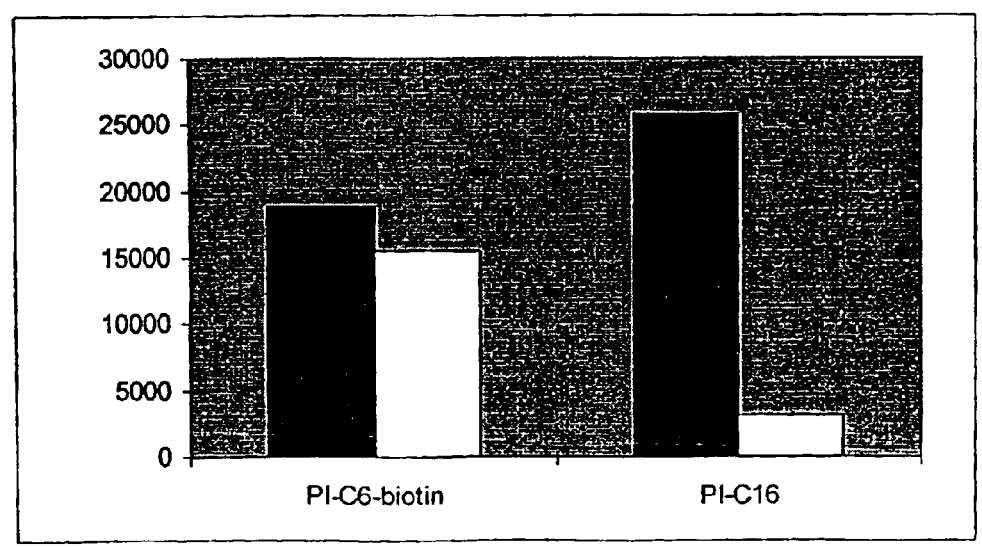

FIG. 11B: Comparison of PI-3K activity using biotinylated short-chain lipids and non-biotinylated long-chain lipids. PI-3K activity was measured using PI-C$_6$-biotin or PI-C$_{16}$ as reaction substrates. The reaction products were bound to streptavidin-coated membranes. The membranes were washed to remove unreactive reactants and were analyzed directly (black bars) or were exposed to chloroform:methanol:water (10:10:3) treatment for lipid re-extraction (white bars).

DETAILED DESCRIPTION OF THE INVENTION

Abbreviations & Definitions:

The following abbreviations and definitions are expressly adopted herein. All terms not provided a definition are to be given their accepted definition in the art:

"Alkyl"=a straight, branched, or cyclic, fully-saturated hydrocarbon radical having the number of carbon atoms designated (i.e., $C_{1-C24}$ means one to 24 carbons); examples include methyl, ethyl, n-propyl, isopropyl, n-butyl, t-butyl, isobutyl, sec-butyl, cyclohexyl, (cyclohexyl)ethyl, cyclopropylmethyl, and the higher homologs and isomers thereof, for example, n-pentyl, n-hexyl, n-heptyl, n-octyl, and the like; an alkyl group will typically contain from 1 to 24 carbon atoms, with those groups having eight or more carbon atoms being preferred in the present invention; a "lower alkyl" is an alkyl group having fewer than eight carbon atoms.

"Alkenyl"=an alkyl group having one or more double bonds or triple bonds; examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

"Alkylcarbonyl"=a carbonyl-containing alkyl radical derived from the corresponding carboxylic acid, e.g. acyl radicals derived from lauric acid, myristic acid, palmitic acid, stearic acid, and the like; will typically contain from 2 to 24 carbon atoms.

"Alkenylcarbonyl"=a carbonyl-containing alkenyl radical derived from the corresponding carboxylic acid, e.g., acyl radicals derived oleic acid, linoleic acid. linolenic acid, eleostearic acid, arachidonic acid, and the like; will typically contain from 2 to 24 carbon atoms.

"Bn"=benzyl.

"BOM"=benzyloxymethyl.

"EDTA"=ethylenediaminetetraacetic acid

"HEPES"=N-2-hydroxyethylpiperazine-N'-2-ethanesulfonic acid

"Lipid kinase/phospholipid kinase"=any enzyme falling within the classification EC 2.7.1.x, where "x" is a variable.

"PDGF"=platelet-derived growth factor.

"Phospholipid phosphatase"=any enzyme falling within the classification EC 3.1.3.x and 3.1.4.x, where "x" is a variable.

"PI"=phosphatidylinositol; an unphosphorylated phosphoinositide (i.e., a phosphoinositide lacking any phosphate groups on the inositol moiety).

"PIK"=generally, phosphoinositide kinase; PI-3-kinase, PI-3K, is the illustrative enzyme.

"PIP"=a phosphorylated phosphoinositide (i.e., a PI having one or more phosphate groups present on the inositol moiety); phosphatidylinositol phosphate.

"PI x,x',x" . . . Pn"=a nomenclature shorthand to designated PIPs, wherein "PI" designates a phosphoinosidite, "x, x', x" . . . " are numerical variables designating the position of phosphate groups on the inositol moiety, "P" designates that the inositol moiety is phosphorylated, and "n" designating the number of phosphate groups present on the inositol moiety.

"PMB"=p-methoxybenzyl.

"PS"=phosphatidylserine.

"Substituted"=a radical including one or more substituents, such as lower alkyl, aryl, acyl, halogen, hydroxy, amino, alkoxy, alkylamino, acylamino, thioamido, acyloxy, aryloxy, aryloxyalkyl, mercapto, thia, aza, oxo, both saturated and unsaturated cyclic hydrocarbons, heterocycles and the like; the substituents may be attached to any carbon of the base moiety.

"Substrate" or "corresponding substrate"=a substrate that can be phosphorylated or dephosphorylated by the enzyme being assayed.

"Solid support"=a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. A solid support can also be a substrate, for example, a chip, wafer, or well.

"TLC"=thin-layer chromatography.

Modifying Substrates to Contain a Binding Moiety:

Substrates for lipid or phospholipid kinases and phosphatases can be obtained commercially from numerous suppliers.

For example, PI's such as D-myo-phosphatidylinositol, D-myo-phosphatidylinositol 3-phosphate, D-myo-phosphatidylinositol 4-phosphate, D-myo-phosphatidylinositol 5-phosphate, D-myo-phosphatidylinositol 3,4-bisphosphate, D-myo-phosphatidylinositol 3,5-bisphosphate, D-myo-phosphatidylinositol 4,5-bisphosphate, D-myo-phosphatidylinositol 3,4,5-trisphosphate, and derivatives thereof, PIK antibodies, and biotin-tagged PI's are available commercially from Echelon Research Laboratories Inc., Salt Lake City, Utah; and Upstate Biotechnology, Lake Placid, N.Y.). The PI's noted above, as well as a host of others, derivatives, and antibodies thereto are also available commercially from A.G. Scientific, Inc., San Diego, Calif.

PI's can also be synthesized using conventional routes from naturally-occurring chiral precursors. For example, inositol head groups can be derived from methyl α-D-glucopyranoside via a Ferrier rearrangement and the diacylglyceryl moieties can be prepared from (+)-isopropylideneglycerol.

The most preferred binding moiety to be affixed to the substate (when such a binding moiety is employed) is a biotin moiety. This is due to biotin's relatively small size, relative ease of chemical manipulation, and its very robust, high-level, and specific binding to avidin and streptavidin.

Biotin can be affixed to an acyl chain of the diacylglycerol portion of a substrate PI via a coupling reaction wherein the biotin is linked via an amide bond to the PI. Note that when affixed to the acyl chain, the biotin does not interfere with recognition of the modified substrate at both the inositol headgroup and the glycerol backbone proximal to the headgroup. This discovery, that a substrate PI can be modified by the addition of a binding moiety such as biotin without interfering with a lipid/phospholipid kinase's or phosphatase's ability to recognize and bind to the substrate, is novel. In short, no prior art known to the inventors describes or suggests that such a modification can be made.

The preferred reaction to affix biotin (or any other binding moiety having an available reactive group) to a PI is analogous to that described in Chen et al. (1996), 61 *J. Org. Chem* 6305–6312, incorporated herein by reference. See also G. D. Prestwich (1996), 29 *Acc. Chem. Res.* 503–513, also incorporated herein by reference.

Briefly, lipid-modified analogs of PI's can be formed by inserting an aminoalkanoyl group at the sn-1 position of the PI. This group then allows for the addition of a binding moiety, preferably biotin, to the end of the acyl chain.

The synthesis, shown in Reaction Scheme 1, follows a convergent approach, beginning with the selective sn-1-O-acylation of a protected chiral glycerol synthon, followed by acylation of the sn-2 position and oxidative deprotection to yield the desired 1,2-O-diacylglycerol derivative.

Reaction with benzyl(N,N,-diisopropylamino) chlorophosphine yields phosphoramidites, which are then condensed with an appropriately protected D-myo-inositol derivative.

REACTION SCHEME 1

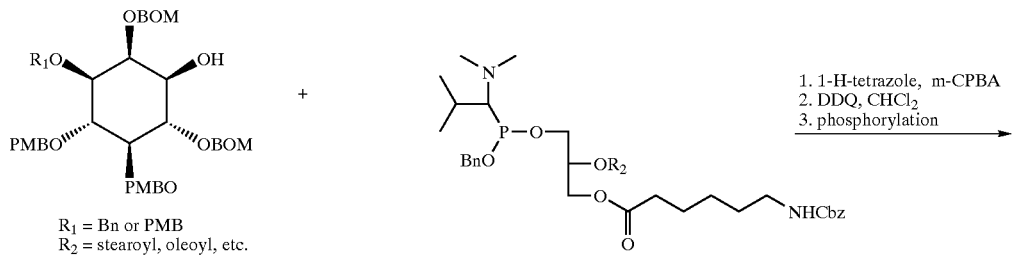

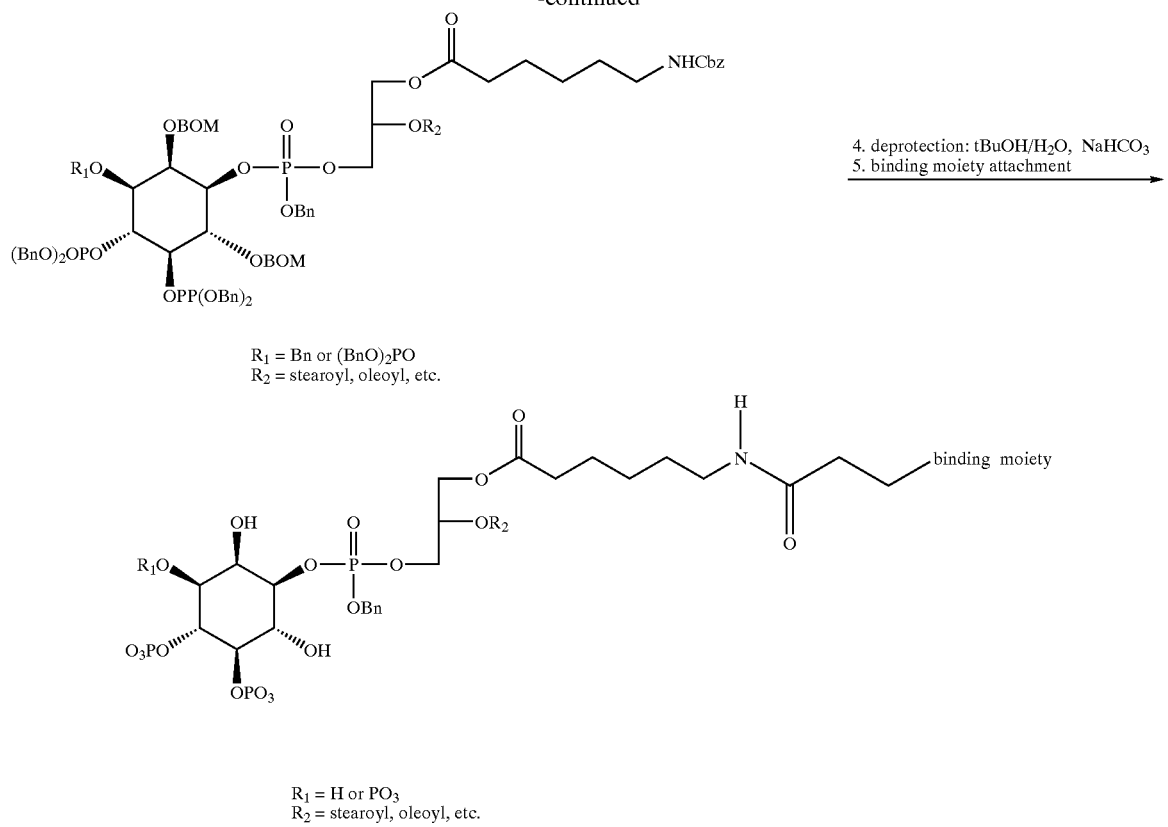

In the intermediate compounds, benzyl (Bn) or benzyloxymethyl (BOM) groups protect the final hydroxyl groups and p-methoxybenzyl (PMB) groups protect the future phosphomonoesters. Deprotection of the PMB groups, followed by phophorylation, hydrogenolysis, and ion exchange chromatography yields the aminoacyl modified PI's.

Attachment of the binding moiety via an ester linkage yields a PI having a binding moiety linked thereto.

Where the binding moiety is something other than biotin, such as an antibody or an antigenic determinant, analogous linking chemistries can be utilized to affix the binding moiety to the acyl chain of the PI.

Binding Matrices:

Where no binding moiety is attached to the substrate, the preferred binding matrix is an aldehyde-activated solid support or substrate, most preferably an aldehyde-activated regenerated cellulose. The preferred matrices are "SARTOBIND"®-brand aldehyde membranes, available commercially from Sartorius Corporation (Edgewood, N.Y., USA and Goettingen, Germany) and SAM2®-brand membranes (described in the following paragraph). Likewise, supports including diethylaminoethyl cellulose and polyvinylidene difluoride can also be used.

Where the binding moiety is biotin, the preferred binding matrix is a support having avidin or streptavidin immobilized thereon. The support may be in the form of a filter, membrane, beads, etc. The most preferred matrices are SAM2®-brand Biotin Capture Membranes or SAM2®-brand 96 Biotin Capture Plates (96-well microtiter format) from Promega Corporation, Madison, Wis. The SAM2®-brand membrane binds biotinylated molecules based on their strong affinity for streptavidin. The process by which the membrane is produced results in a high density of streptavidin on the membrane filter matrix, promoting rapid, quantitative capture of biotinylated substrates. In addition, the SAM2®-brand membrane has been optimized for low non-specific binding. Using the 96 well plate format allows washes to be performed using a vacuum manifold or a commercially available plate washer.

Where the binding moiety is an antibody or antigenic determinant, the preferred binding matrix is an affinity matrix having immobilized thereon a compound which binds strongly and specifically with the binding moiety.

Enzymes That Can Be Assayed:

The subject assay can be used to detect and measure the presence of any lipid or phospholipid kinase or phosphatase. In short, any enzyme whose catalytic activity transfers a phosphate group to a lipid or phospholipid substrate, or any enzyme whose catalytic activity removes a phosphate group from a lipid orphospholipid substrate, can be assayed using the present invention.

More specifically, the subject assay can be used to determine the presence and/or activity of any lipid or phospholipid kinase falling within the Enzyme Classification (EC) 2.7.1.x (where x is a variable), including, without limitation, EC 2.7.1.1 hexokinase, EC 2.7.1.2 glucokinase, EC 2.7.1.3 ketohexokinase, EC 2.7.1.4 fructokinase, EC 2.7.1.5 rhamnulokinase, EC 2.7.1.6 galactokinase, EC 2.7.1.7 mannokinase, EC 2.7.1.8 glucosamine kinase, EC 2.7.1.10 phosphoglucokinase, EC 2.7.1.11 6-phosphofructokinase, EC 2.7.1.12 gluconokinase, EC 2.7.1.13 dehydrogluconokinase, EC 2.7.1.14 sedoheptulokinase, EC 2.7.1.15 ribokinase, EC 2.7.1.16 ribulokinase, EC 2.7.1.17 xylulokinase, EC 2.7.1.18 phosphoribokinase, EC 2.7.1.19 phosphoribulokinase, EC 2.7.1.20 adenosine kinase, EC 2.7.1.21 thymidine kinase, EC 2.7.1.22 ribosylnicotinamide kinase, EC 2.7.1.23 NAD kinase, EC 2.7.1.24 dephospho-CoA kinase, EC 2.7.1.25 adenylyl-sulfate kinase, EC 2.7.1.26 riboflavin kinase, EC 2.7.1.27 erythritol kinase, EC 2.7.1.28 triokinase, EC 2.7.1.29 glycerone kinase, EC 2.7.1.30 glycerol kinase, EC 2.7.1.31 glycerate kinase, EC 2.7.1.32 choline kinase, EC 2.7.1.33 pantothenate kinase, EC 2.7.1.34 pantetheine kinase, EC 2.7.1.35 pyridoxal kinase, EC 2.7.1.36 mevalonate kinase, EC 2.7.1.37 protein kinase, EC 2.7.1.38 phosphorylase kinase, EC 2.7.1.39 homoserine kinase, EC 2.7.1.40 pyruvate kinase, EC 2.7.1.41 glucose-1-phosphate phosphodismutase, EC 2.7.1.42 riboflavin phosphotransferase, EC 2.7.1.43 glucuronokinase, EC 2.7.1.44 galacturonokinase, EC 2.7.1.45 2-dehydro-3-deoxygluconokinase, EC 2.7.1.46 L-arabinokinase, EC 2.7.1.47 D-ribulokinase, EC 2.7.1.48 uridine kinase, EC 2.7.1.49 hydroxymethylpyrimidine kinase, EC 2.7.1.50 hydroxyethylthiazole kinase, EC 2.7.1.51 L-fuculokinase, EC 2.7.1.52 fucokinase, EC 2.7.1.53 L-xylulokinase, EC 2.7.1.54 D-arabinokinase, EC 2.7.1.55 allose kinase, EC 2.7.1.56 1-phosphofructokinase, EC 2.7.1.58 2-dehydro-3-deoxygalactonokinase, EC 2.7.1.59 N-acetylglucosamine kinase, EC 2.7.1.60 N-acylmannosamine kinase, EC 2.7.1.61 acyl-phosphate-hexose phosphotransferase, EC 2.7.1.62 phosphoramidate-hexose phosphotransferase, EC 2.7.1.63 polyphosphate-glucose phosphotransferase, EC 2.7.1.64 inositol 1-kinase, EC 2.7.1.65 scyllo-inosamine 4-kinase, EC 2.7.1.66 undecaprenol kinase, EC 2.7.1.67 1-phosphatidylinositol 4-kinase, EC 2.7.1.68 1-phosphatidylinositol-4-phosphate 5-kinase, EC 2.7.1.69 protein-Np-phosphohistidine-sugarphosphotransferase, EC 2.7.1.70 protamine kinase, EC 2.7.1.71 shikimate kinase, EC 2.7.1.72 streptomycin 6-kinase, EC 2.7.1.73 inosine kinase, EC 2.7.1.74 deoxycytidine kinase, EC 2.7.1.75 (now EC 2.7.1.21), EC 2.7.1.76 deoxyadenosine kinase, EC 2.7.1.77 nucleoside phosphotransferase, EC 2.7.1.78 polynucleotide 5'-hydroxyl-kinase, EC 2.7.1.79 diphosphate-glycerol phosphotransferase, EC 2.7.1.80 diphosphate-serine phosphotransferase, EC 2.7.1.81 hydroxylysine kinase, EC 2.7.1.82 ethanolamine kinase, EC 2.7.1.83 pseudouridine kinase, EC 2.7.1.84 alkylglycerone kinase, EC 2.7.1.85 b-glucoside kinase, EC 2.7.1.86 NADH2 kinase, EC 2.7.1.87 streptomycin 3"-kinase, EC 2.7.1.88 dihydrostreptomycin-6-phosphate 3'a-kinase, EC 2.7.1.89 thiamine kinase, EC 2.7.1.90 diphosphate-fructose-6-phosphate 1-phosphotransferase, EC 2.7.1.91 sphinganine kinase, EC 2.7.1.92 5-dehydro-2-deoxygluconokinase, EC 2.7.1.93 alkylglycerol kinase, EC 2.7.1.94 acylglycerol kinase, EC 2.7.1.95 kanamycin kinase, EC 2.7.1.96 (included in EC 2.7.1.86), EC 2.7.1.97 (identical to EC 2.7.1.125), EC 2.7.1.99 {pyruvate dehydrogenase (lipoamide)} kinase, EC 2.7.1.100 5-methylthioribose kinase, EC 2.7.1.101 tagatose kinase, EC 2.7.1.102 hamamelose kinase, EC 2.7.1.103 viomycin kinase, EC 2.7.1.104 diphosphate-protein phosphotransferase, EC 2.7.1.105 6-phosphofructo-2-kinase, EC 2.7.1.106 glucose-1,6-bisphosphate synthase, EC 2.7.1.107 diacylglycerol kinase, EC 2.7.1.108 dolichol kinase, EC 2.7.1.109 {hydroxymethylglutaryl-CoA reductase (NADPH2)} kinase, EC 2.7.1.110 dephospho-{reductase kinase} kinase, EC 2.7.1.111 (now EC 2.7.1.128), EC 2.7.1.112 protein-tyrosine kinase, EC 2.7.1.113 deoxyguanosine kinase, EC 2.7.1.114 AMP-thymidine kinase, EC 2.7.1.115{3-methyl-2-oxobutanoate dehydrogenase (lipoamide)} kinase, EC 2.7.1.116{isocitrate dehydrogenase (NADP)} kinase, EC 2.7.1.117 myosin-light-chainkinase, EC 2.7.1.118 ADP-thymidine kinase, EC 2.7.1.119 hygromycin-B kinase, EC 2.7.1.120 caldesmon kinase, EC 2.7.1.121 phosphoenolpyruvate-glycerone phosphotransferase, EC 2.7.1.122 xylitol kinase, EC 2.7.1.123 Ca2+/calmodulin-dependent protein kinase, EC 2.7.1.124 {tyrosine 3-monooxygenase} kinase, EC 2.7.1.125 rhodopsin kinase, EC 2.7.1.126 b-adrenergic-receptor kinase, EC 2.7.1.127 1-D-myo-inositol-trisphosphate 3-kinase, EC 2.7.1.128 {acetyl-CoA carboxylase} kinase, EC 2.7.1.129 myosin-heavy-chain kinase, EC 2.7.1.130 tetraacyldisaccharide 4'-kinase, EC 2.7.1.131 low-density-lipoprotein kinase, EC 2.7.1.132 tropomyosin kinase, EC 2.7.1.133 inositol-trisphosphate 6-kinase, EC 2.7.1.134 inositol-tetrakisphosphate 1-kinase, EC 2.7.1.135 tau-protein kinase, EC 2.7.1.136 macrolide 2'-kinase, EC 2.7.1.137 1-phosphatidylinositol 3-kinase, EC 2.7.1.138 ceramide kinase, EC 2.7.1.139 inositol-trisphosphate 5-kinase, EC 2.7.1.140 inositol-tetrakisphosphate 5-kinase, EC 2.7.1.141 {RNA-polymerase}-subunit kinase, EC 2.7.1.142 glycerol-3-phosphate-glucose phosphotransferase, EC 2.7.1.143 diphosphate-purine nucleoside kinase, EC 2.7.1.144 tagatose-6-phosphate kinase, and EC 2.7.1.145 deoxynucleoside kinase.

Preferred kinases which can be assayed using the subject assay include EC 2.7.1.137 (1-phosphatidylinositol 3-kinase, referred to herein as PI-3K), EC 2.7.1.67 (1-phosphatidylinositol 4-kinase), EC 2.7.1.68 (1-phosphatidylinositol-4-phosphate kinase, also called diphosphoinositide kinase or PIP kinase), 1-phosphatidylinositol 5-kinase (PI-5K), and the like.

Regarding phosphatases, the subject assay can be used to determine the presence and/or activity of any lipid or phospholipid phosphatase falling within the Enzyme Classification (EC) 3.1.3.x and EC 3.1.4.x (where x is a variable), including, without limitation, EC 3.1.3.1 alkaline phosphatase, EC 3.1.3.2 acid phosphatase, EC 3.1.3.3 phosphoserine phosphatase, EC 3.1.3.4 phosphatidate phosphatase, EC 3.1.3.5 5'-nucleotidase, EC 3.1.3.6 3'-nucleotidase, EC 3.1.3.7 3'(2'),5'-bisphosphate nucleotidase, EC 3.1.3.8 3-phytase, EC 3.1.3.9 glucose-6-phosphatase, EC 3.1.3.10 glucose-1-phosphatase, EC 3.1.3.11 fructose-bisphosphatase, EC 3.1.3.12 trehalose-phosphatase, EC 3.1.3.13 bisphosphoglycerate phosphatase, EC 3.1.3.14 methylphosphothioglycerate phosphatase, EC 3.1.3.15 histidinol-phosphatase, EC 3.1.3.16 phosphoprotein phosphatase, EC 3.1.3.17{phosphorylase}phosphatase, EC 3.1.3.18 phosphoglycolate phosphatase, EC 3.1.3.19 glycerol-2-phosphatase, EC 3.1.3.20 phosphoglycerate phosphatase, EC 3.1.3.21 glycerol-1-phosphatase, EC 3.1.3.22 mannitol-1-phosphatase, EC 3.1.3.23 sugar-phosphatase, EC 3.1.3.24 sucrose-phosphatase, EC 3.1.3.25 inositol-1(or 4)-monophosphatase, EC 3.1.3.26 6-phytase, EC 3.1.3.27 phosphatidylglycerophosphatase, EC 3.1.3.28 ADPphosphoglycerate phosphatase, EC 3.1.3.29 N-acylneuraminate-9-phosphatase, EC 3.1.3.30 deleted, included in EC 3.1.3.31, EC 3.1.3.31 nucleotidase, EC 3.1.3.32 polynucleotide 3'-phosphatase, EC 3.1.3.33 polynucleotide 5'-phosphatase, EC 3.1.3.34 deoxynucleotide 3'-phosphatase, EC 3.1.3.35 thymidylate 5'-phosphatase, EC 3.1.3.36 phosphatidylinositol-bisphosphatase, EC 3.1.3.37 sedoheptulose-bisphosphatase, EC 3.1.3.38 3-phosphoglycerate phosphatase, EC 3.1.3.39 streptomycin-6-phosphatase, BC 3.1.3.40 guanidinodeoxy-scyllo-inositol-4-phosphatase, EC 3.1.3.41 4-nitrophenylphosphatase, EC 3.1.3.42 {glycogen-synthase-D} phosphatase, EC 3.1.3.43 {pyruvate dehydrogenase (lipoamide)}-phosphatase, EC 3.1.3.44 {acetyl-CoA carboxylate}-phosphatase, EC 3.1.3.45 3-doxy-manno-octulosonate-8-phosphatase, EC 3.1.3.46 fructose-2,6-bisphosphate 2-phosphatase, EC 3.1.3.47 {hydroxymethylglutaryl-CoA reductase (NADPH)}-phosphatase, EC 3.1.3.48 protein-tyrosine-phosphatase, EC 3.1.3.49 {pyruvate kinase}-phosphatase, EC 3.1.3.50 sorbitol-6-phosphatase, EC 3.1.3.51 dolichyl-phosphatase, EC 3.1.3.52 {3-methyl-2-oxobutanoate dehydrogenase (lipoamide)}-phosphatase, EC 3.1.3.53 myosin-light-chain-phosphatase, EC 3.1.3.54 fructose-2,6-bisphosphate 6-phosphatase, EC 3.1.3.55 caldesmon-phosphatase, EC 3.1.3.56 inositol-1,4,5-trisphosphate 5-phosphatase, EC 3.1.3.57 inositol-1,4-bisphosphate 1-phosphatase, EC 3.1.3.58 sugar-terminal-phosphatase, EC 3.1.3.59 alkylacetylglycerophosphatase, EC 3.1.3.60 phosphoenolpyruvate phosphatase, EC 3.1.3.61 inositol-1,4,5-trisphosphate 1-phosphatase, EC 3.1.3.62 inositol-1,3,4,5-tetrakisphosphate 3-phosphatase, EC 3.1.3.63 2-carboxy-D-arabinitol-1-phosphatase, EC 3.1.3.64 phosphatidylinositol-3-phosphatase, EC 3.1.3.65 inositol-1,3-bisphosphate 3-phosphatase, EC 3.1.3.66 inositol-3,4-bisphosphate 4-phosphatase, EC 3.1.3.67 phosphatidylinositol-3,4,5-trisphosphate 3-phosphatase, EC 3.1.3.68 2-deoxyglucose-6-phosphatase, EC 3.1.4.1 phosphodiesterase I, EC 3.1.4.2 glycerophosphocholine phosphodiesterase, EC 3.1.4.3 phospholipase C, EC 3.1.4.4 phospholipase D, EC 3.1.4.10 1-phosphatidylinositol phosphodiesterase, EC 3.1.4.11 1-phosphatidylinositol-4,5-bisphosphate phosphodiesterase, EC 3.1.4.12 sphingomyelin phosphodiesterase, EC 3.1.4.13 serine-ethanolaminephosphate phosphodiesterase, EC 3.1.4.14 {acyl-carrier-protein}phosphodiesterase, EC 3.1.4.15 adenylyl-{glutamate-ammonia ligase}hydrolase, EC 3.1.4.16 2',3'-cyclic-nucleotide 2'-phosphodiesterase, EC 3.1.4.17 3',5'-cyclic-nucleotide phosphodiesterase, EC 3.1.4.35 3',5'-cyclic-GMP phosphodiesterase, EC 3.1.4.36 1,2-cyclic-inositol-phosphate phosphodiesterase, EC 3.1.4.37 2',3'-cyclic-nucleotide 3'-phosphodiesterase, EC 3.1.4.38 glycerophosphocholine cholinephosphodiesterase, EC 3.1.4.39 alkylglycerophosphoethanolamine phosphodiesterase, EC 3.1.4.40 CMP-N-acylneuraminate phosphodiesterase, EC 3.1.4.41 sphingomyelin phosphodiesterase D, EC 3.1.4.42 glycerol-1,2-cyclic-phosphate 2-phosphodiesterase, EC 3.1.4.43 glycerophosphoinositol inositolphosphodiesterase, EC 3.1.4.44 glycerophosphoinositol glycerophosphodiesterase, EC 3.1.4.45 N-acetylglucosamine-1-phosphodiester a-N-acetylglucosaminidase, EC 3.1.4.46 glycerophosphodiester phosphodiesterase, EC 3.1.4.47 variant-surface-glycoprotein phospholipase C, EC 3.1.4.48 dolichylphosphate-glucose phosphodiesterase, EC 3.1.4.49 dolichylphosphate-mannose phosphodiesterase, EC 3.1.4.50 glycoprotein phospholipase D, EC 3.1.4.51 glucose-1-phospho-D-mannosylglycoprotein phosphodiesterase, Preferred phosphatases which can be assayed using the subject assay include EC 3.1.3.27 (phosphatidylglycerophosphatase), EC 3.1.3.36 (phosphatidylinositol bisphosphatase; triphosphoinositide phosphatase), EC 3.1.3.64 (phosphatidylinositol-3-phosphatase), EC 3.1.3.67 (phosphatidylinositol-3,4,5-trisphosphate 3-phosphatase), EC 3.1.4.10 (1-phosphatidylinositol phosphodiesterase; monophosphatidylinositol phosphodiesterase; phosphatidylinositol phospholipase C), EC 3.1.4.11 (1-phosphatidylinositol-4,5-bisphosphate phosphodiesterase, triphosphoinositide phosphodiesterase), phosphatidylinositol 3,4,5-triphosphate 5-phosphatase, and the like.

The assay can also be extended to assay for the presence and or activity of phosphorylases.

Kits:

The present invention is also directed to kits that utilize the assay described herein. A basic kit for measuring the presence and/or activity of a lipid/phospholipid kinase or phosphatase enzyme includes a vessel containing a natural, semi-synthetic, or wholly synthetic enzyme substrate and/or a modified enzyme substrate having a binding moiety attached thereto, the modified substrate having specific reactivity to the enzyme to be assayed. The kit also contains a binding matrix that specifically adsorbs or otherwise binds to and immobilizes the binding moiety on the modified substrate. Instructions for use of the kit may also be included. The kit may also include an appropriate amount of reaction buffer disposed in a suitable container.

"Instructions for use," is a tangible expression describing the reagent concentration or at least one assay method parameter such as the relative amount of reagent and sample to be admixed, maintenance time periods for reagent/sample admixtures, temperature, buffer conditions, and the like. The instructions for use are suitable to enable an analyst to carry out the desired assay.

Where the modified substrate includes the preferred binding moiety, biotin, the preferred embodiment of the kit includes a biotin-binding matrix comprising avidin or streptavidin molecules immobilized on an inert support such as filter disks, beads, plates, or a soluble matrix.

The amounts of the various reagents in the kits can be varied depending on various factors, such as the optimum sensitivity of the assay, the number of assays to be performed, etc.

It is within the scope of the invention to provide manual test kits or test kits for use in automated analyzers.

The Assay Protocol:

Referring now to FIG. 1, which is a flow chart comparing a prior art method (left-hand column) to the preferred embodiment of the present invention (right-hand column), a number of benefits of the present invention are immediately apparent:

Addressing the present invention first, the most immediate advantage is that the lipids do not have to be dried from an organic solvent. Instead, the reaction solution is simply spotted directly onto the binding matrix. The enzyme is added to the bound substrate and the reaction run for a specified period of time. The reaction is then stopped, the membrane is rinsed, and the amount of label retained on the matrix is measured.

In stark contrast, the conventional approach requires that the lipid substrates must be dried from an organic solvent (normally chloroform/methanol), and resuspended (normally by sonication) in an aqueous reaction solution. The enzymatic reaction to be studied is then performed in the aqueous reaction solution. After the reaction is complete, the lipid products must be extracted back into chloroform/methanol for analysis. Thus, the conventional approach entails a number of manual separation steps that are both time-consuming, reagent-consuming, and not particularly amenable to automation. The need for these drying and extraction steps are minimized or eliminated entirely in the subject invention.

The assay protocol of the present invention is best illustrated via a number of Examples. The Examples are included solely to provide a more complete understanding of the invention described and claimed herein. The Examples do not limit the scope of the claimed invention in any way.

EXAMPLE 1

The following Example demonstrates that PI-3 kinase and PI4P-5 kinase, members from two distinct structural families of phosphoinositide kinases (PI and PIP kinases, respectively), can act to add a phosphate to a phospholipid substrate that has been immobilized on a solid support. Moreover, this Example demonstrates that this can be accomplished directly from organic solutions where the reaction substrates exist as monomers (i.e., individual lipid molecules), rather than from an aqueous phase where the reaction substrates exist as vesicles or micelles.

Further, this Example shows that the product lipids remain bound to the matrix during washing procedures, thereby providing an easy means to separate the products of the enzymatic reaction from unreacted reactants, enzyme, and other non-product ingredients of the reaction solution.

The data generated according to the present invention are compared with analogous data generated using the conventional phospholipid extraction procedure exemplified in FIG. 1. In the conventional approach, the substrates for enzyme modification are presented in the form of vesicles or micelles in an aqueous reaction solution. After the enzymatic reaction (which takes place in the aqueous solution), the product lipids are separated from the other reaction components by extracting the products back into an organic phase, normally chloroform/methanol. The product lipids partition into the organic phase, while the other reaction components remain in the aqueous phase phase. A comparative flow chart of the prior art method and the subject invention is presented in FIG. 1.

Lipids, 10 µg of PI4,5P$_2$+20 µg of PS, were dissolved in chloroform:methanol (2:1) and loaded onto "SAM2"-brand membranes for PI-3K activity measurements. Likewise, 10 µg of PI4P was loaded onto "SAM2"-brand membranes for PI4P-5K activity measurements. The membranes were air dried and a reaction mixture containing 50 mM HEPES/NaOH, pH7.5, 100 mM NaCl, 10 mM MgCl$_2$, 20 ng partially-purified PI-3K or 10 ng of purified PI4P-5K, 50 µM ATP supplemented with 1 µCi of γ-$^{32}$P-ATP was added onto the membrane containing the immobilized lipids.

Following incubation at room temperature, the reactions were stopped with 7.5 M guanidine chloride and the membranes were washed with 2M NaCl, followed by 2 M NaCl/1% H$_3$PO$_4$. The washed membranes were dried and subjected to scintillation counting. The obtained data are presented in FIG. 2A (white bars).

Figure 2A:
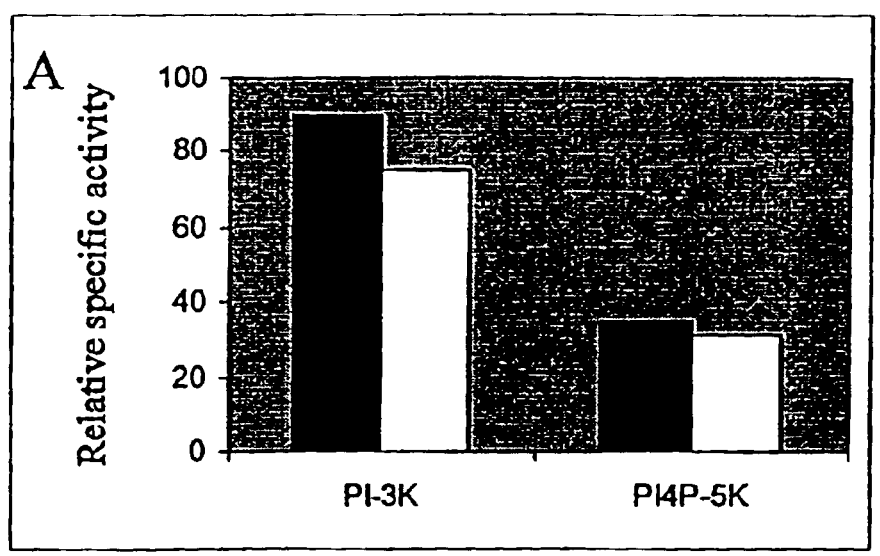
FIG. 2A: Comparison of PIK activity measurements: present invention vs. conventional phospholipid extraction procedure. Assays were performed using partially-purified PI-3K (500 ng/ml) for 40 minutes or purified PI4P-5K (250 ng/ml) for 20 minutes. For PI-3K activity measurements, PI4,5P$_2$ (10 μg)+PS (20 μg) was used as reaction substrate. The PI4P-5K reaction was carried out using PI4P (10 μg) as reaction substrate. Samples were processed using the conventional phospholipid extraction procedure illustrate in FIG. 1 (black bars) or according to the present invention (white bars).

In the conventional phospholipid extraction procedure, the same amount of lipids indicated above were dried under nitrogen and re-suspended by sonication in 50 mM HEPES/NaOH, pH 7.5 buffer containing 1 mM EDTA. Then the reaction mixture was added to sonicated lipids and the reaction was carried out in aqueous solution. The reaction was stopped with 1N HCl, lipids were extracted as indicated in FIG. 1 and analyzed. The data are shown in FIG. 2A (black bars).

Figure 2B:
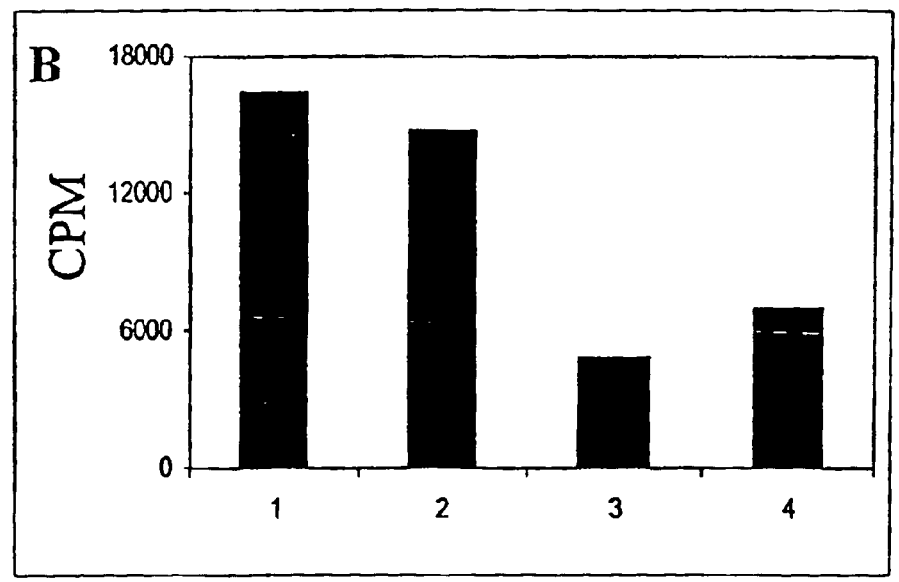
FIG. 2B: Comparison of PT-K activity measurements: present invention vs. standard phospholipid extraction procedure. Assays were done using immuno-precipitated PI-3K from liver tissue (500 μg) for 60 min. All the reactions were carried out at room temperature using PIP$_2$ (10 μg)+PS (20

To generate immunoprecipitated enzyme as used in FIG. 2B, livers were removed from rats after ether anesthesia. The livers were cut into small pieces and homogenized. The homogenate was centrifuged at 10,000×g for 10 minutes. The supernatant was centrifuged at 15,000×g for 1 hour. The supernatant was then titrated to pH 5.75 by drop-wise addition of 1 M acetic acid. After stirring for 10 minutes at 4° C., the solution was centrifuged at 10,000×g for 10 minutes. The pellet was re-suspended in buffer containing 50 mM HEPES/NaOH, pH 7.5.

Then, 6 µl of anti PI-3 kinase p85 rabbit polyclonal IgG (Upstate Biotechnology, Lake Placid, N.Y.) were added to each tube containing the lysed cell solution and the tubes were incubated overnight at 4° C. Then 100 µl of protein A sepharose CL-4B (Pharmacia, Peapack, N.J.) was added to each tube and they were further incubated for 2 hours at 4° C. The sepharose/antibody/antigen complex (the "complex") was then pelleted by centrifugation, the supernatant removed and the complex washed twice with PBS containing 1% NP-40 and 10% glycerol, three times with 100 mM Tris/HCl (pH 7.5) containing 500 mM NaCl and 100 µM Na$_3$VO$_4$ and twice with 10 mM Tris/HCl containing 100 mM NaCl, 1 mM EDTA, 100 µM Na$_3$VO$_4$. Then 50 µl of 10 mM Tris/HCl (pH 7.5) containing 100 mM NaCl was added to the complex and this solution was then referred to as the immunoprecipitated PI-3 kinase enzyme.

Immunoprecipitated PI-3 K was assayed as described above for purified PI-3K with lipid substrates immobilized on "SAM"-brand membranes. All reactions were carried out at room temperature using 10 µg PI4,5P2+20 µg PS (FIG. 2B, bars 3 and 4) or 50 µg PI (FIG. 2B, bars 1 and 2) as reaction substrates.

EXAMPLE 2

An assays analogous to that depicted in Example 1 can be assembled to assay for the presence and/or activity of lipid and phospholipid phosphatases, such as phosphatidylinositol-3,4,5-trisphosphate 3-phosphatase.

Here, the substrate bearing the binding moiety is phosphorylated with a known amount of {γ-$^{32}$P} ATP.

The reaction components were the same as described in Example 1. The reaction components were applied directly to a "SAM2"-brand membrane and the reaction run for the specified period of time and then terminated. The results of the experiment are generated by measuring the decreased amount of radiation present in the products which adhere to the binding matrix as compared to the radioactivity present in the reactants.

EXAMPLE 3

In resting cells, PI-3K is located in the cytosol. However, upon cell stimulation, the enzyme is recruited to the plasma membrane where it is associated with particular receptors and is involved in further propagation of the signal. This example illustrates that the described method allows to measure PI-3K activity associated with activated receptor. 3T3 NIH cells (0.5×10$^7$ cells) were starved overninght in serum-free medium. PDGF (50 ng/ml) was added to the starved cells and the induction was carried out for 5 min at 37° C. Following the PDGF induction, cells were washed once with PBS while on the plate, scraped into PBS, transferred to a centrifuge tube, pelleted by centrifugation. The cell pellet was lysed and activated receptor-PI-3K complex was iminunoprecipitated using anti-phosphotyrosine specific antibodies. The PI-3K reaction was run for 60 min using PI4,5P$_2$ (10 µg) as substrate, immobilized on "SAM2"-brand membranes, together with 20 µg of carrier lipid (PS). The increase in PI-3K activity upon stimulation with PDGF is shown in FIG. 3. This Example clearly indicates that the present invention enables cells to be monitored for activation and also enables the analysis of PI-3K activity associated with activated receptors.

EXAMPLE 4

This Example illustrates the dependence of PIK activity on the amount of lipid substrate loaded onto the binding matrix. In FIG. 4A, PI-3K activity was measured using PI-3K from Alexis (12.5 µg/ml) for 60 min at room temperature (using the protocol of Example 1, with any modifications noted). In FIG. 4B, PI-5K activity was measured using purified PI-5K (125 ng/ml) for 60 min at room temperature. In addition to lipid substrates, all samples contained 10 μg of PS loaded on the membrane.

As shown in FIG. 4A, the reaction yields a linear response from 0 to roughly 6 μg of substrate. The reaction then reaches a saturation point at roughly 7 μg of $PIP_2$. Beyond this concentration of substrate, the presence of additional substrate does not result in higher radioactivity incorporation in the formed product. FIG. 4B, which illustrates the results for PI-5K, shows that the enzyme activity expressed as CPM count remains unchanged in going from PI4P concentrations from 1 to 10 μg, thus indicating that at these substrate levels, the reaction is already saturated.

EXAMPLE 5

This Example illustrates the linear detection of PIP-5K activity using the present invention. Assays were performed using the described protocol (Example 1) with 3 μl of lipid mixture containing 1 μg of PI4P and 10 μg of PS in chloroform/methanol 2:1 spotted onto a pre-numbered membrane square.

In FIGS. 5A and 5B, the PI-5K activity was measured at different time points (0, 2.5, 5, 10, and 20 min) using 4 ng of purified protein. In FIGS. 5C and 5D, PI-5K activity was measured for 10 min using different protein concentrations (0, 50, 125, 200, 250 ng/ml). The reaction products were analyzed by phosphorimaging (FIGS. 5A and 5C) or by scintillation counting (FIGS. 5B and 5D). As is clearly illustrated by this series of figures, the assay protocol yields linear time-dependent results (FIGS. 5A and 5B) and concentration-dependent results (FIGS. 5C and 5D). Between 20 pmol and 1.2 nmol of formed product can be detected using the subject invention.

EXAMPLE 6

In this Example, linear detection of PI-3K activity was assayed using the present invention. Assays were performed using the described protocol with 5 μl of PI (25 μg) in chloroform/methanol 2:1 spotted onto a well of modified SAM-brand membrane 96-well plate (Promega). Assays were performed using different amounts of partially purified PI-3K: 1 ng (light green); 2 ng (dark green); 4 ng (yellow); 8 ng (orange); 16 ng (red). Based on obtained scintillation counts, the specific activity has been calculated and shown in FIG. 6A). The calculated initial reaction rate for different amount of protein is shown in FIG. 6B. This Example shows that the subject method yields linear detection of enzyme over a broad concentration range.

EXAMPLE 7

This Example is a comparison of reaction products detected using the present invention versus the conventional phospholipid extraction procedure outlined in FIG. 1. In FIG. 10, activities were assessed using 1 μg of PI4P+10 μg of PS as reaction substrates and purified PI-5K as an enzyme source. The reaction was carried out for 0 (lanes 3, 4) and 30 minutes (lanes 1, 2). The reaction was performed using a conventional phospholipid extraction procedure (lanes 2, 4) or according to the subject invention (lanes 1, 3). When using the subject invention, following reaction performed on membrane sheets, the lipids were re-extracted for TLC analysis.

The results show that the products formed using the present invention yield useful information on enzymatic activity, information that is comparable to the widely-used conventional assay described earlier.

EXAMPLE 8

This Example demonstrates the reproducibility of the subject invention. Assays were performed using:

FIG. 7A: partially purified PI-3K (500 ng/ml) and $PIP_2$ (10 μg)+PS (20 μg) as lipid substrates for 40 minutes FIG. 7B: PI-5K (125 ng/ml) and PI4P (1 μg)+PS(10 μg) for 15 minutes FIG. 7C: PI-5K (125 ng/ml) and PI4P (1 μg) for 60 minutes.

All assays were performed at room temperature using 1 μCi of $^{32}$P-ATP.

In FIG. 7C, the reactions were carried out on three different plates (samples 1–4; 5–8; 9–12, respectively). In each plate the reactions were done in triplicates at three different locations. Each point represents the average of three independent reactions. Yellow bars show the average of 9 points done on the same plate.

As is clearly shown by this set of experiments, the method is highly reproducible.

EXAMPLE 9

This Example illustrates that the products formed by the enzymatic reaction are due solely to the presence of active enzyme. This is shown by the loss of products formed when the reaction is run in the presence of an inhibitor that is specific to PI-3K. A reaction was run with partially purified PI-3K for different periods of time in the presence (triangles) or absence (diamonds) of PI-3K inhibitor wortmannin (final concentration 100 nM). See FIG. 8. As shown in FIG. 8, the present method yielded greatly reduced radiolabeled product as expressed in CPM values when the assay was performed in the presence of the PI-3K inhibitor.

EXAMPLE 10

This Example illustrates the reaction specificity toward lipid substrates. Here, a reaction was performed with purified PI-5K (125 ng/ml) for 15 min at room temperature using different lipid substrates: PI3,4P (lane 1); PI3,5P (lane 2) and PI4,5P2 (Lane 3). PI3,5P (lane 2) and PI4,5P (lane 3), which already have a phosphate group in the 5-position, are not substrates for PI-5K, an enzyme that functions to catalyze the addition of a phosphate group to the 5-position of a suitable substrate. Thus, as clearly shown in FIG. 9, the assay generate appropriate results and thus demonstrates specificity for enzyme substrates. PI3,4P (lane 1) is a suitable substrate for the PI-5K enzyme and shows the expected, corresponding CPM values, indicating that the enzyme has, in fact, specifically phosphorylated these substrates.

EXAMPLE 11

The following Example demonstrates that PI-3 kinase (PI-3K) can act to add a phosphate to a biotinylated phospholipid when the phospholipid is biotinylated in such a way as not to interfere with the interaction between the enzyme and the biotinylated substrate. The biotin group is attached to the lipid substrate, preferably to the end of the lipid chain. This Example also demonstrates that a streptavidin matrix is capable of separating the biotinylated, phosphorylated product from non-biotinylated components of the reaction mixture to allow for detection and quantitation of the product.

Lipids: 30 μg of short-chain PI4P-$C_8$, biotin-modified short-chain PI4P-$C_6$-biotin, and long-chain PI4P-$C_{16}$ were dried under vacuum in the presence of 10 μg carrier lipid (PS) in separate tubes. The dried lipids were dissolved in 50 mM HEPES/NaOH, pH 7.5+1 mM EDTA buffer and subjected to sonication for 5 min. This solution is referred to as the "prepared substrate."

The following kinase reactions were then assembled:

4 μl of 100 mM $MgCl_2$

20 μl of prepared substrate

1 μl of purified PI4P-5K or PI-3K
11 μl 50 mM HEPES/NaOH+100 mM NaCl buffer
4 μl of 0.5 mM ATP containing 1 μCi $^{32}$P-ATP The reactions were carried out for 15 minutes at room temperature. In FIG. 11A, following the reaction, lipids were extracted and analyzed on TLC to show that biotinylated lipids can be modified by PI-kinases. In FIG. 11B, 25% of the reaction mixture was loaded on "SAM2"-brand membranes, the membranes were washed and then analyzed directly (black bars) or the membranes were exposed for additional treatment with chloroform/methanol/water (10:10:3) to remove and separate modified from unmodified lipids (white bars).

This Example indicates that membrane-bound lipids remain attached to the matrix during separation procedures and thereby allows separation of reaction products from other reaction components. However, natural lipids bound to the membranes can be removed under defined conditions, for example, following membrane treatment with chloroform:methanol:water (10:10:3). Thus, the reaction products can be subjected to more detailed structural analysis if needed.

What is claimed is:

1. A method for assaying presence, activity, or both, of an enzyme, the method comprising:
   (a) under conditions which render the enzyme active, reacting the enzyme with a corresponding substrate, the substrate including a binding moiety, for a time sufficient to yield phosphorylated product when assaying enzymes that catalyze transfer of a phosphate group to a lipid or phospholipid substrate, or dephosphorylated product when assaying enzymes that catalyze removal of a phosphate group from a phospholipid substrate, the product also including the binding moiety; and
   (b) contacting the product with a binding matrix specific for the binding moiety; whereby product is specifically fixed to the matrix; and then
   (c) analyzing the matrix for presence of, amount of, or both the presence and the amount of the product, whereby the presence, the activity, or both the presence and activity of the enzyme is determined.

2. The method of claim 1, wherein the binding moiety is biotin and the binding matrix is avidin or streptavidin immobilized on a solid support.

3. The method of claim 1, wherein the binding moiety is an antigenic determinant and the binding matrix is an antibody specific for the antigenic determinant, the antibody being immobilized on a solid support.

4. The method of claim 1, wherein the binding moiety is an antibody, and the binding matrix is an antigenic determinant specific to the antibody, the antigenic determinant being immobilized on a solid support.

5. The method of claim 1, wherein the binding moiety is an antibody, and the binding matrix is an anti-antibody specific for the antibody, the anti-antibody being immobilized on a solid support.

6. The method of claim 1, wherein the enzyme assayed is classified within an enzyme classification selected from the group consisting of EC 2.7.1.67, EC 2.7.1.68, and EC 2.7.1.137.

7. The method of claim 6, wherein in step (b), the product is contacted with a binding matrix comprising an aldehyde-activated support.

8. The method of claim 6, wherein in step (b), the product is contacted with a binding matrix comprising an aldehyde-activated regenerated cellulose support.

9. The method of claim 6, wherein in step (a), the enzyme is reacted with the corresponding substrate in the presence of labeled phosphate groups, and in step (c), the matrix is analyzed by determining the presence, the amount, or the presence and amount, of labeled phosphate groups fixed to the matrix.

10. The method of claim 9, wherein in step (a), the enzyme is reacted with the corresponding substrate in the presence of $^{32}$P-labeled phosphate groups, and in step (c),the matrix is analyzed using a scintillation counter or a phosphoimager.

11. The method of claim 6, wherein in step (a), the enzyme is reacted with a substrate of formula:

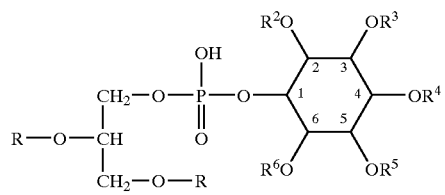

wherein each R is independently an unsubstituted or substituted $C_2$ to $C_{24}$ alkyl, alkenyl, alkylcarbonyl, or alkenylcarbonyl group, and $R^2,R^3$, $R^4$, $R^5$ and are selected from the group consisting of hydrogen and phosphate, provided that not all of $R^2,R^3$, $R^4$, $R^5$ and $R^6$ are simultaneously phosphate.

12. The method of claim 1, wherein the enzyme assayed is classified within an enzyme classification selected from the group consisting of EC 3.1.3.27, EC 3.1.3.36, EC 3.1.3.64, EC 3.1.3.67, and EC 3.1.4.13.

13. The method of claim 12, wherein in step (b), the product is contacted with a binding matrix comprising an aldehyde-activated support.

14. The method of claim 12, wherein in step (b), the product is contacted with a binding matrix comprising an aldehyde-activated regenerated cellulose support.

15. The method of claim 12, wherein in step (a), the enzyme is reacted with the corresponding substrate in the presence of labeled phosphate groups, and in step (c), the matrix is analyzed by determining the presence, the amount, or the presence and amount, of labeled phosphate groups fixed to the matrix.

16. The method of claim 15, wherein in step (a), the enzyme is reacted with the corresponding substrate in the presence of $^{32}$P-labeled phosphate groups, and in step (c),the matrix is analyzed using a scintillation counter or a phosphoimager.

17. The method of claim 12, wherein in step (a), the enzyme is reacted with a substrate of formula:

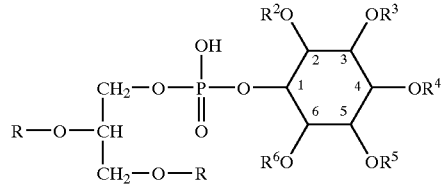

wherein each R is independently an unsubstituted or substituted $C_2$ to $C_{24}$ alkyl, alkenyl, alkylcarbonyl, or alkenylcarbonyl group, and $R^2,R^3$, $R^4$, $R^5$ and $R^6$ are selected from the group consisting of hydrogen and phosphate, provided that not all of $R^2,R^3$, $R^4$, $R^5$ and $R^6$ are simultaneously hydrogen.

* * * * *